US012396693B2

United States Patent
Wolff et al.

(10) Patent No.: US 12,396,693 B2
(45) Date of Patent: Aug. 26, 2025

(54) SYSTEMS AND METHODS FOR CONFIRMING TISSUE SPECIMENS REMOVED USING CONTRAST-ENHANCED X-RAY IMAGING

(71) Applicant: HOLOGIC, INC., Marlborough, MA (US)

(72) Inventors: David Wolff, Marlborough, MA (US); Stewart Schiffman, Marlborough, MA (US)

(73) Assignee: Hologic, Inc., Marlborough, MA (US)

( * ) Notice: Subject to any disclaimer, the term of this patent is extended or adjusted under 35 U.S.C. 154(b) by 347 days.

(21) Appl. No.: 18/245,148

(22) PCT Filed: Aug. 31, 2021

(86) PCT No.: PCT/US2021/048450
§ 371 (c)(1),
(2) Date: Mar. 13, 2023

(87) PCT Pub. No.: WO2022/060566
PCT Pub. Date: Mar. 24, 2022

(65) Prior Publication Data
US 2024/0016461 A1    Jan. 18, 2024

Related U.S. Application Data

(60) Provisional application No. 63/079,028, filed on Sep. 16, 2020.

(51) Int. Cl.
*A61B 6/00*      (2024.01)
*A61B 6/04*      (2006.01)
(Continued)

(52) U.S. Cl.
CPC ............ *A61B 6/502* (2013.01); *A61B 6/0414* (2013.01); *A61B 6/4035* (2013.01); *A61B 6/481* (2013.01);
(Continued)

(58) Field of Classification Search
None
See application file for complete search history.

(56) References Cited

U.S. PATENT DOCUMENTS

| 4,038,988 A | 8/1977 | Perisse |
| 4,134,012 A | 1/1979 | Smallbone et al. |

(Continued)

FOREIGN PATENT DOCUMENTS

| DE | 20 2019 106 995 | 1/2020 |
| EP | 2277445 | 1/2011 |

(Continued)

OTHER PUBLICATIONS

PCT International Preliminary Report on Patentability in Application PCT/US2021/048450, mailed Mar. 30, 2023, 9 pages.

(Continued)

*Primary Examiner* — Hoon K Song
(74) *Attorney, Agent, or Firm* — Merchant & Gould P.C.

(57) ABSTRACT

For a biopsy guided by contrast-enhanced x-ray imaging, a breast imaging system may image a patient's breast subsequent to injection of contrast agent to locate a site for biopsy and/or position a biopsy device relative to the site. Once a tissue specimen is removed from the site for diagnostic evaluation, a confirmation that the specimen was removed from an intended area of interest for biopsy is performed using the systems and methods described herein. For example, the breast imaging system and/or a separate specimen imaging system may capture high and low energy images of the specimen, subtract the low energy image from (Continued)

the high energy image to generate a subtracted image of the specimen, and determine, based on the subtracted image, that the contrast agent is present within the specimen to confirm the site from which the specimen was removed is the intended site for biopsy.

20 Claims, 10 Drawing Sheets

(51) Int. Cl.
*A61B 6/40* (2024.01)
*A61B 6/50* (2024.01)
*G06T 7/00* (2017.01)

(52) U.S. Cl.
CPC .. *G06T 7/0014* (2013.01); *G06T 2207/10116* (2013.01); *G06T 2207/30068* (2013.01); *G06T 2207/30096* (2013.01)

(56) References Cited

U.S. PATENT DOCUMENTS

| | | |
|---|---|---|
| 4,306,570 A | 12/1981 | Matthews |
| 4,549,554 A | 10/1985 | Markham |
| 4,658,834 A | 4/1987 | Blankenship et al. |
| 4,802,195 A | 1/1989 | Wojcienchowski |
| 4,803,639 A | 2/1989 | Steele |
| 4,837,795 A | 6/1989 | Garrigus |
| 4,852,560 A | 8/1989 | Hermann, Jr. |
| 5,023,894 A | 6/1991 | Yamashita |
| 5,023,895 A | 6/1991 | McCroskey |
| 5,256,160 A | 10/1993 | Clement |
| 5,427,742 A | 6/1995 | Holland |
| 5,456,689 A | 10/1995 | Kresch et al. |
| 5,491,344 A | 2/1996 | Kenny et al. |
| 5,505,210 A | 4/1996 | Clement |
| 5,526,822 A | 6/1996 | Burbank et al. |
| 5,541,856 A | 7/1996 | Hammermeister |
| 5,575,293 A | 11/1996 | Miller et al. |
| 5,609,827 A | 3/1997 | Russell |
| 5,754,621 A | 5/1998 | Suzuki |
| 5,872,828 A | 2/1999 | Niklason |
| 5,983,125 A | 11/1999 | Alfano et al. |
| 6,017,316 A | 1/2000 | Ritchart et al. |
| 6,032,673 A | 3/2000 | Savage et al. |
| 6,058,159 A | 5/2000 | Conway |
| 6,163,590 A | 12/2000 | Wilkins |
| 6,207,111 B1 | 3/2001 | Weinberg |
| 6,225,107 B1 | 5/2001 | Nagle |
| 6,234,672 B1 | 5/2001 | Tomasetti et al. |
| 6,322,522 B1 | 11/2001 | Zimmon |
| 6,403,035 B1 | 6/2002 | Caratsch et al. |
| 6,485,436 B1 | 11/2002 | Truckai et al. |
| 6,535,284 B1 | 3/2003 | Hajduk et al. |
| 6,646,721 B2 | 11/2003 | Compter |
| 6,882,700 B2 | 4/2005 | Wang |
| 6,899,850 B2 | 5/2005 | Haywood |
| 6,999,554 B2 | 2/2006 | Mertelmeier |
| 7,110,490 B2 | 9/2006 | Eberhard |
| 7,166,113 B2 | 1/2007 | Arambula |
| 7,175,612 B2 | 2/2007 | Felix et al. |
| 7,298,816 B2 | 11/2007 | Moore |
| 7,397,894 B2 | 7/2008 | Nakai |
| 7,453,979 B2 | 11/2008 | Sendai |
| 7,546,925 B1 | 6/2009 | Zuk, Jr. |
| 7,573,977 B2 | 8/2009 | Tsujita |
| 7,616,801 B2 | 11/2009 | Gkanatsios et al. |
| 7,662,109 B2 | 2/2010 | Hibner |
| 7,692,144 B2 | 4/2010 | Watanabe |
| 7,697,661 B2 | 4/2010 | Souchay |
| 7,708,462 B2 | 5/2010 | Fujiwara |
| 7,715,523 B2 | 5/2010 | Lafferty |
| 7,753,857 B2 | 7/2010 | Hibner |
| 7,758,601 B2 | 7/2010 | Heywang-Koebrunner et al. |
| 7,817,773 B2 | 10/2010 | Stanton |
| 7,826,588 B2 | 11/2010 | Eliasson |
| 7,835,490 B2 | 11/2010 | Ramsauer |
| 7,854,705 B2 | 12/2010 | Pawluczyk et al. |
| 7,856,081 B2 | 12/2010 | Peschmann |
| 7,858,038 B2 | 12/2010 | Andreyko et al. |
| 7,867,173 B2 | 1/2011 | Hibner et al. |
| 7,869,563 B2 | 1/2011 | DeFreitas et al. |
| 7,881,427 B2 | 2/2011 | Kalender et al. |
| 7,881,428 B2 | 2/2011 | Jing et al. |
| 7,885,378 B2 | 2/2011 | Kopans |
| 7,972,062 B2 | 7/2011 | Nicolosi |
| 8,038,347 B2 | 10/2011 | Manak |
| 8,038,627 B2 | 10/2011 | Hibner |
| 8,050,735 B2 | 11/2011 | Feke |
| 8,052,616 B2 | 11/2011 | Andrisek et al. |
| 8,162,140 B2 | 4/2012 | Hansen |
| 8,177,728 B2 | 5/2012 | Hibner et al. |
| 8,213,570 B2 | 7/2012 | Panesar |
| 8,217,357 B2 | 7/2012 | Stein et al. |
| 8,235,913 B2 | 8/2012 | Hibner et al. |
| 8,284,896 B2 | 10/2012 | Singh |
| 8,532,745 B2 | 9/2013 | DeFreitas et al. |
| 8,553,837 B2 | 10/2013 | Johansson |
| 8,565,374 B2 | 10/2013 | DeFreitas et al. |
| 8,702,623 B2 | 4/2014 | Parihar |
| 8,741,232 B2 | 6/2014 | Baysal |
| 8,764,679 B2 | 7/2014 | Miller et al. |
| 8,787,522 B2 | 7/2014 | Smith et al. |
| 8,838,207 B2 | 9/2014 | Nakayama et al. |
| 8,873,716 B2 | 10/2014 | Ren et al. |
| 8,911,381 B2 | 12/2014 | Hibner et al. |
| 8,923,603 B2 | 12/2014 | Weston |
| 8,956,306 B2 | 2/2015 | Hibner |
| 8,971,484 B2 | 3/2015 | Beckmann |
| 8,983,030 B2 | 3/2015 | Ookawa |
| 9,020,579 B2 | 4/2015 | Smith et al. |
| 9,066,706 B2 | 6/2015 | DeFreitas et al. |
| 9,068,920 B2 | 6/2015 | Churilla |
| 9,129,715 B2 | 9/2015 | Adler |
| 9,188,696 B2 | 11/2015 | Schafer |
| 9,234,855 B2 | 1/2016 | Watanabe |
| 9,277,895 B2 | 3/2016 | Hara |
| 9,322,790 B2 | 4/2016 | Ookawa |
| 9,326,755 B2 | 5/2016 | Fiebig |
| 9,329,139 B2 | 5/2016 | Itou |
| 9,341,546 B2 | 5/2016 | Stuke |
| 9,347,894 B2 | 5/2016 | Sims |
| 9,492,130 B2 | 11/2016 | Flagle et al. |
| 9,498,175 B2 | 11/2016 | Stein et al. |
| 9,549,709 B2 | 1/2017 | DeFreitas et al. |
| 9,557,281 B2 | 1/2017 | Badawi et al. |
| 9,642,581 B2 | 5/2017 | Lowe |
| 9,668,711 B2 | 6/2017 | Smith et al. |
| 9,733,167 B2 | 8/2017 | Wismueller |
| 9,750,484 B2 | 9/2017 | Finke et al. |
| 9,861,327 B2 | 1/2018 | Yasuda et al. |
| 9,865,424 B2 | 1/2018 | Ikeda |
| 9,901,320 B2 | 2/2018 | DeFreitas et al. |
| 9,943,850 B2 | 4/2018 | Purdy |
| 9,953,799 B2 | 4/2018 | Hakoda |
| 10,008,298 B2 | 6/2018 | King |
| 10,010,296 B2 | 7/2018 | Basu |
| 10,078,093 B2 | 9/2018 | Flagle |
| 10,098,216 B2 | 10/2018 | Kabumoto |
| 10,105,709 B2 | 10/2018 | Purdy |
| 10,145,806 B2 | 12/2018 | Tanaka |
| 10,190,997 B2 | 1/2019 | Aoki |
| 10,194,875 B2 | 2/2019 | DeFreitas et al. |
| 10,201,331 B2 | 2/2019 | Fleming |
| 10,322,412 B2 | 6/2019 | Purdy |
| 10,393,678 B2 | 8/2019 | Watanabe |
| 10,488,351 B2 | 11/2019 | Butani |
| 10,489,964 B2 | 11/2019 | Wang |
| 10,542,951 B2 | 1/2020 | Klausz et al. |
| 10,561,387 B2 | 2/2020 | Smith et al. |
| 10,631,809 B2 | 4/2020 | Noh |
| 10,646,178 B2 | 5/2020 | Butani |
| 10,652,990 B2 | 5/2020 | Butani |

(56) References Cited

U.S. PATENT DOCUMENTS

| | | |
|---|---|---|
| 10,670,545 B2 | 6/2020 | Butani |
| 10,705,030 B2 | 7/2020 | Watanabe |
| 10,709,396 B2 | 7/2020 | Lou |
| 10,729,399 B2 | 8/2020 | Butani |
| 10,729,403 B2 | 8/2020 | DeFreitas et al. |
| 10,753,836 B2 | 8/2020 | O'Driscoll et al. |
| 10,792,003 B2 | 10/2020 | Smith et al. |
| 10,809,208 B2 | 10/2020 | Yashima |
| 10,827,989 B2 | 11/2020 | Vancamberg et al. |
| 10,830,712 B2 | 11/2020 | Butani |
| 10,905,385 B2 | 2/2021 | DeFreitas et al. |
| 10,921,265 B2 | 2/2021 | Butani |
| 10,937,161 B2 | 3/2021 | Butani |
| 11,020,066 B2 | 6/2021 | Butani |
| 11,039,803 B1 | 6/2021 | Butani |
| 11,083,426 B2 | 8/2021 | DeFreitas |
| 11,162,909 B2 | 11/2021 | Butani |
| 11,191,502 B2 | 12/2021 | Smith et al. |
| 11,207,036 B2 | 12/2021 | Butani |
| 11,246,551 B2 | 2/2022 | Butani |
| 11,317,881 B2 | 5/2022 | Purdy |
| 11,358,149 B2 | 6/2022 | Purdy |
| 11,478,206 B2 | 10/2022 | Smith et al. |
| 11,566,981 B2 | 1/2023 | O'Driscoll |
| 11,617,548 B2 | 4/2023 | DeFreitas et al. |
| 11,730,434 B2 | 8/2023 | DeFreitas |
| 11,877,877 B2 | 1/2024 | Purdy |
| 2002/0007188 A1 | 1/2002 | Arambula |
| 2002/0145722 A1 | 10/2002 | Compter |
| 2002/0193656 A1 | 12/2002 | Ravins et al. |
| 2003/0087423 A1 | 5/2003 | Haywood |
| 2003/0216730 A1 | 11/2003 | Barry et al. |
| 2004/0022350 A1 | 2/2004 | Gregerson et al. |
| 2004/0174031 A1 | 9/2004 | Rasmussen |
| 2004/0218716 A1 | 11/2004 | Freifeld |
| 2005/0051723 A1 | 3/2005 | Neagle et al. |
| 2005/0065453 A1 | 3/2005 | Shabaz et al. |
| 2005/0112034 A1 | 5/2005 | McCormick |
| 2005/0124913 A1 | 6/2005 | Damarati |
| 2005/0148842 A1 | 7/2005 | Wang |
| 2006/0074343 A1 | 4/2006 | Hibner |
| 2006/0116603 A1 | 6/2006 | Shibazaki et al. |
| 2006/0173266 A1 | 8/2006 | Pawluczyk et al. |
| 2007/0106176 A1 | 5/2007 | Mark et al. |
| 2007/0116612 A1 | 5/2007 | Williamson |
| 2007/0166834 A1 | 7/2007 | Williamson et al. |
| 2007/0237684 A1 | 10/2007 | Hansen |
| 2007/0239067 A1 | 10/2007 | Hibner et al. |
| 2007/0270714 A1 | 11/2007 | Cushner et al. |
| 2008/0004545 A1 | 1/2008 | Garrison |
| 2008/0082021 A1 | 4/2008 | Ichikawa |
| 2008/0132805 A1 | 6/2008 | Heywang-Koebrunner et al. |
| 2008/0214955 A1 | 9/2008 | Speeg et al. |
| 2008/0221480 A1 | 9/2008 | Hibner et al. |
| 2008/0228103 A1 | 9/2008 | Ritchie et al. |
| 2008/0249434 A1 | 10/2008 | Hashimshony et al. |
| 2009/0088663 A1 | 4/2009 | Miller et al. |
| 2009/0088666 A1 | 4/2009 | Miller et al. |
| 2009/0131818 A1 | 5/2009 | Speeg et al. |
| 2009/0131820 A1 | 5/2009 | Speeg |
| 2009/0131823 A1 | 5/2009 | Andreyko et al. |
| 2009/0171243 A1 | 7/2009 | Hibner et al. |
| 2009/0171244 A1 | 7/2009 | Ning |
| 2009/0213987 A1 | 8/2009 | Stein |
| 2010/0080346 A1 | 4/2010 | Kalender et al. |
| 2010/0081964 A1 | 4/2010 | Mark |
| 2010/0152611 A1 | 6/2010 | Parihar |
| 2010/0160824 A1 | 6/2010 | Parihar |
| 2010/0160826 A1 | 6/2010 | Parihar |
| 2010/0191145 A1 | 7/2010 | Lafferty |
| 2010/0317997 A1 | 12/2010 | Hibner |
| 2011/0123074 A1 | 5/2011 | Nie |
| 2011/0142201 A1 | 6/2011 | Eberhard et al. |
| 2011/0285837 A1 | 11/2011 | Bello |
| 2012/0014504 A1 | 1/2012 | Jang et al. |
| 2012/0051514 A1 | 3/2012 | Sims et al. |
| 2012/0053484 A1 | 3/2012 | Parks |
| 2012/0116246 A1 | 5/2012 | Hibner |
| 2012/0123295 A1 | 5/2012 | Sanbuichi |
| 2012/0245485 A1 | 9/2012 | Hibner |
| 2013/0053724 A1 | 2/2013 | Fiebig |
| 2013/0231585 A1 | 9/2013 | Flagle |
| 2014/0039343 A1 | 2/2014 | Mescher |
| 2014/0051986 A1 | 2/2014 | Zhao et al. |
| 2014/0065656 A1 | 3/2014 | Baysal |
| 2014/0072104 A1 | 3/2014 | Jacobsen et al. |
| 2014/0198893 A1 | 7/2014 | Badawi et al. |
| 2014/0257135 A1 | 9/2014 | DeFreitas |
| 2014/0276209 A1 | 9/2014 | Hibner |
| 2015/0083893 A1 | 3/2015 | Wismueller |
| 2015/0131773 A1 | 5/2015 | Lowe et al. |
| 2015/0209017 A1 | 7/2015 | Fleming |
| 2016/0211045 A1 | 7/2016 | Jeon et al. |
| 2017/0131311 A1 | 5/2017 | Flagle |
| 2017/0309063 A1 | 10/2017 | Wang |
| 2017/0336706 A1 | 11/2017 | Wang |
| 2018/0045660 A1 | 2/2018 | Yashima |
| 2018/0168523 A1 | 6/2018 | Vancamberg et al. |
| 2018/0249985 A1 | 9/2018 | DeFreitas et al. |
| 2019/0054217 A1 | 2/2019 | Axon |
| 2019/0072463 A1 | 3/2019 | O'Driscoll |
| 2019/0130563 A1 | 5/2019 | Vecchio et al. |
| 2019/0167869 A1 | 6/2019 | Willard |
| 2019/0285558 A1 | 9/2019 | DeFreitas |
| 2019/0346471 A1 | 11/2019 | Flagle |
| 2020/0029927 A1 | 1/2020 | Wilson et al. |
| 2020/0061622 A1 | 2/2020 | Purdy |
| 2020/0085393 A1 | 3/2020 | Zhang et al. |
| 2020/0187923 A1 | 6/2020 | Safir |
| 2020/0268331 A1 | 8/2020 | Purdy |
| 2020/0352543 A1 | 11/2020 | DeFreitas et al. |
| 2020/0386657 A1 | 12/2020 | O'Driscoll |
| 2021/0259649 A1* | 8/2021 | Milioni De Carvalho ............... G06T 7/337 |
| 2022/0015729 A1 | 1/2022 | Purdy et al. |
| 2022/0015731 A1 | 1/2022 | Liu |
| 2022/0039766 A1 | 2/2022 | DeFreitas |
| 2022/0071583 A1* | 3/2022 | Chmeissani Raad ... G01T 1/241 |
| 2022/0110597 A1 | 4/2022 | Chen |
| 2022/0133252 A1 | 5/2022 | Smith et al. |
| 2022/0296189 A1 | 9/2022 | Purdy |
| 2022/0331808 A1 | 10/2022 | Purdy |
| 2023/0012310 A1 | 1/2023 | Stango |
| 2023/0014922 A1 | 1/2023 | DeFreitas |
| 2023/0121010 A1 | 4/2023 | Smith et al. |
| 2023/0136395 A1 | 5/2023 | Chen |
| 2023/0172572 A1 | 6/2023 | Bumdra |
| 2023/0204473 A1 | 6/2023 | O'Driscoll |
| 2023/0355200 A1* | 11/2023 | Ren ........ A61B 6/032 |
| 2023/0404499 A1 | 12/2023 | DeFreitas |
| 2024/0315676 A1 | 9/2024 | Chen |
| 2024/0359187 A1 | 10/2024 | Purdy |

FOREIGN PATENT DOCUMENTS

| | | |
|---|---|---|
| EP | 2007287 | 6/2016 |
| EP | 3143937 | 3/2017 |
| GB | 2018601 | 10/1979 |
| JP | 2006-346179 | 12/2006 |
| JP | 2014-526937 | 10/2014 |
| JP | 2015-085056 A | 5/2015 |
| JP | 2015-520402 | 7/2015 |
| JP | 2016-154878 | 9/2016 |
| JP | 2017099928 | 6/2017 |
| JP | 6320717 B2 | 5/2018 |
| WO | 8101363 | 5/1981 |
| WO | 2007021905 | 2/2007 |
| WO | 2008/025146 | 3/2008 |
| WO | 2009/120206 | 10/2009 |
| WO | 2010/028208 | 3/2010 |
| WO | 2011/140374 | 11/2011 |
| WO | 2012/074885 | 6/2012 |
| WO | 2013/166497 | 11/2013 |
| WO | 2017/060726 | 4/2017 |

(56) References Cited

FOREIGN PATENT DOCUMENTS

| WO | 2018/183086 | 10/2018 |
| WO | 2018/204710 | 11/2018 |
| WO | 2019/051496 | 3/2019 |
| WO | 2019/085342 | 5/2019 |
| WO | 2019/216766 | 11/2019 |
| WO | 2020/106888 | 5/2020 |
| WO | 2021/202455 A1 | 10/2021 |

OTHER PUBLICATIONS

Watanabe, M. et al., "The quantitative analysis of thin specimens: a review of progress from the Cliff-Lorimer to the new zeta-factor methods", Journal of Microscopy, vol. 221, No. 2, Feb. 1, 2006, p. 91.

Basak Erguvan-Dogan et al., "Specimen Radiography in Confirmation of MRI-Guided Needle Localization and Surgical Excision of Breast Lesions", American Journal of Roentgenology, American Roentgen Ray Society, vol. 187, No. 2: 339-344 (2006).

International Search Report and Written Opinion for PCT/US2021/048450 (Nov. 29, 2021).

* cited by examiner

SYSTEMS AND METHODS FOR CONFIRMING TISSUE SPECIMENS REMOVED USING CONTRAST-ENHANCED X-RAY IMAGING

CROSS-REFERENCE TO RELATED APPLICATIONS

This application is a National Stage Application of PCT/US2021/048450, filed on Aug. 31, 2021, which claims the benefit of priority to U.S. Provisional Patent Application No. 63/079,028, filed on Sep. 16, 2020, the disclosures of which are incorporated by reference in their entireties. To the extent appropriate, a claim of priority is made to each of the above disclosed applications.

BACKGROUND

If abnormal breast tissue (e.g., a lesion) is discovered within an area of a patient's breast through screening procedures, a breast biopsy may be performed to remove a core sample of breast tissue from the area as a specimen for diagnostic evaluation. Upon removal, it is critical to confirm that the specimen includes the lesion to be diagnostically evaluated.

In a breast biopsy guided by standard x-ray imaging (e.g., mammography and/or tomosynthesis imaging procedures without contrast enhancement), the lesion may be located based on an identification of clusters of microcalcifications, where the microcalcifications are calcium deposits within the breast that absorb x-rays causing the microcalcifications to be opaque within the captured x-ray images. Following biopsy, the removed specimen may then be confirmed by imaging the specimen at low energy and identifying a presence of these clusters of microcalcifications within the low energy image of the specimen. The specimen is typically imaged in a cabinet x-ray system that is a separate from a breast imaging system used for guiding the breast biopsy. Alternatively, the specimen may be imaged using a specimen imaging modality of the breast imaging system (e.g., may be imaged on the gantry).

Certain lesions may be difficult to visualize using standard x-ray imaging. In such scenarios, the biopsy may instead be guided by contrast-enhanced x-ray imaging (e.g., contrast-enhanced mammography and/or tomosynthesis) to locate the lesions, particularly when the lesions are characterized by abnormal vascularity. For example, during a contrast-enhanced image guided biopsy procedure, the location of a lesion in the breast may be identified in three dimensions using information extracted from stereotactic pairs of contrast-enhanced dual energy subtracted two-dimensional images or contrast-enhanced dual energy subtracted three-dimensional images. However, when contrast-enhanced x-ray imaging is implemented to locate the lesion within the breast, the low energy images of the specimen captured by traditional specimen imaging systems cannot successfully confirm that the specimen was removed from the intended area for biopsy (e.g., that the specimen includes the lesion).

It is with respect to these and other general considerations that the aspects disclosed herein have been made. Also, although relatively specific problems may be discussed, it should be understood that the examples should not be limited to solving the specific problems identified in the background or elsewhere in this disclosure.

SUMMARY

Examples of the present disclosure describe systems and methods for confirming tissue specimens removed using contrast-enhanced x-ray imaging. In an example aspect, the technology relates to a method that includes receiving a specimen of breast tissue removed from a site of a patient's breast subsequent to an injection of a vascular contrast agent into the patient, capturing a high energy image of the specimen, capturing a low energy image of the specimen, subtracting the low energy image from the high energy image to generate a subtracted image of the specimen, and determining, based on the subtracted image of the specimen, that the contrast agent is present within the specimen to confirm the site from which the specimen was removed is an intended area of interest for biopsy.

In an example, a weighting factor may be applied to the low energy image to generate a weighted low energy image, and the weighted low energy image may be subtracted from the high energy image. Prior to the subtracting, a first gain controlled image may be generated from the high energy image, a second gain controlled image may be generated from the low energy image, and the second gain controlled image may be subtracted from the first gain controlled image to generate the subtracted image of the specimen.

In another example, the contrast agent may be opaque in the high energy image of the specimen and translucent in the low energy image of the specimen such that when the low energy image is subtracted from the high energy image, the presence of the contrast agent in the specimen is visible in the subtracted image of the specimen. The intended area of interest for the biopsy may be an area including at least a portion of potentially abnormal breast tissue.

In another aspect, the technology relates to a system for confirming tissue specimens removed using contrast-enhanced x-ray imaging. The system may include an image capturing system, a specimen retaining apparatus, and an image processing system communicatively coupled to the image capturing system. The image capturing system may include at least an x-ray source and a detector for imaging a specimen of breast tissue removed during a biopsy from a site of a patient's breast subsequent to an injection of a vascular contrast agent into the patient. The apparatus may retain the specimen of breast tissue after removal, where the apparatus is positioned relative to the x-ray source and the detector to enable the image capturing system to capture images of the specimen. The image processing system may include at least a processor and a memory coupled to the processor and storing instructions. When executed by the processor, the stored instructions cause the processor to receive, from the image capturing system, a captured high energy image of the specimen and a captured low energy image of the specimen, subtract the low energy image from the high energy image to generate a subtracted image of the specimen, and determine, based on the subtracted image of the specimen, the contrast agent is present within the specimen to confirm the site from which the specimen was removed is an intended area of interest for the biopsy.

In an example, the system may be a breast imaging system, and the image capturing system may be further operable to image the patient's breast subsequent to the injection of the vascular contrast agent and prior to the biopsy to one or more of locate the site and position a biopsy device relative to the site. The image capturing system may include a single x-ray source. When the x-ray source is the single x-ray source, the image capturing system may further include one or more filters to enable the image capturing system to image both the patient's breast and the specimen, and capture both the high energy and low energy images. The apparatus may be one or more of a specimen container positioned on the breast imaging system, a specimen container that is removably coupleable to the breast imaging system and independently rotatable relative to the x-ray source, and a reservoir of a vacuum assisted biopsy assembly that is independently positionable relative to the x-ray source and the detector.

In another example, the system may be a specimen imaging system separate from a breast imaging system. The image capturing system may include at least two x-ray sources, where a first of the at least two x-ray sources may be operable to emit an x-ray beam at a high energy to capture the high energy image of the specimen, and a second of the at least two x-ray sources may be operable to emit an x-ray beam at a low energy to capture the low energy image of the specimen. The apparatus may include a first positioning member and a second positioning member that surround the specimen and are secured to one another to retain the specimen therebetween.

In a further example, the contrast agent may be opaque in the high energy image of the specimen and translucent in the low energy image of the specimen such that when the low energy image is subtracted from the high energy image, the presence of the contrast agent in the specimen is visible in the subtracted image of the specimen.

In a further example aspect, the technology relates to a breast imaging system for confirming tissue specimens removed using contrast-enhanced x-ray imaging. The breast imaging system may include an image capturing system, a specimen retaining apparatus, and an image processing system communicatively coupled to the image capturing system. The image capturing system may include at least an x-ray source, one or more filters, and a detector. The image capturing system may be operable to capture, subsequent to an injection of a vascular contrast agent into the patient and prior to a biopsy, a high energy image and a low energy image of a patient's breast to one or more of locate a site for the biopsy and position a biopsy device relative to the site, and capture, upon removal of a specimen of breast tissue from the site during the biopsy, a high energy image and a low energy image of the specimen. The apparatus may retain the specimen upon removal and may be positioned relative to the x-ray source and the detector to enable the image capturing system to capture the high energy image and the low energy image of the specimen. The image processing system may include at least a processor and a memory coupled to the processor and storing instructions. When executed by the processor, the stored instructions cause the processor to receive, from the image capturing system, the captured high energy image of the specimen and the captured low energy image of the specimen, subtract the low energy image from the high energy image to generate a subtracted image of the specimen, and determine, based on the subtracted image of the specimen, that the contrast agent is present within the specimen to confirm the site from which the specimen was removed is an intended area of interest for the biopsy.

In an example, at least one of the filters is a specimen imaging filter implemented to enable imaging of the specimen that includes at least one aperture defined therein, and the specimen imaging filter blocks a portion of an emitted x-ray beam from the x-ray source so that the at least one aperture defines a path of the emitted x-ray beam towards the detector. The filters may also include a high energy acquisition filter to enable capture of the high energy images. The breast imaging system may further include a filter assembly including a plurality of filter slots, where each of the one or more filters may be disposed within a slot of the plurality of filter slots.

In another example, the apparatus is one or more of a specimen container positioned on the breast imaging system, a specimen container that is removably coupleable to the breast imaging system and independently rotatable relative to the x-ray source, and a reservoir of a vacuum assisted biopsy assembly that is independently positionable relative to the x-ray source and the detector. The contrast agent may be opaque in the high energy image of the specimen and translucent in the low energy image of the specimen such that when the low energy image is subtracted from the high energy image, the presence of the contrast agent in the specimen is visible in the subtracted image of the specimen.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Additional aspects, features, and/or advantages of examples will be set forth in part in the description which follows and, in part, will be apparent from the description, or may be learned by practice of the disclosure.

BRIEF DESCRIPTION OF THE DRAWINGS

Non-limiting and non-exhaustive examples are described with reference to the following figures.

DETAILED DESCRIPTION

Figure 1:
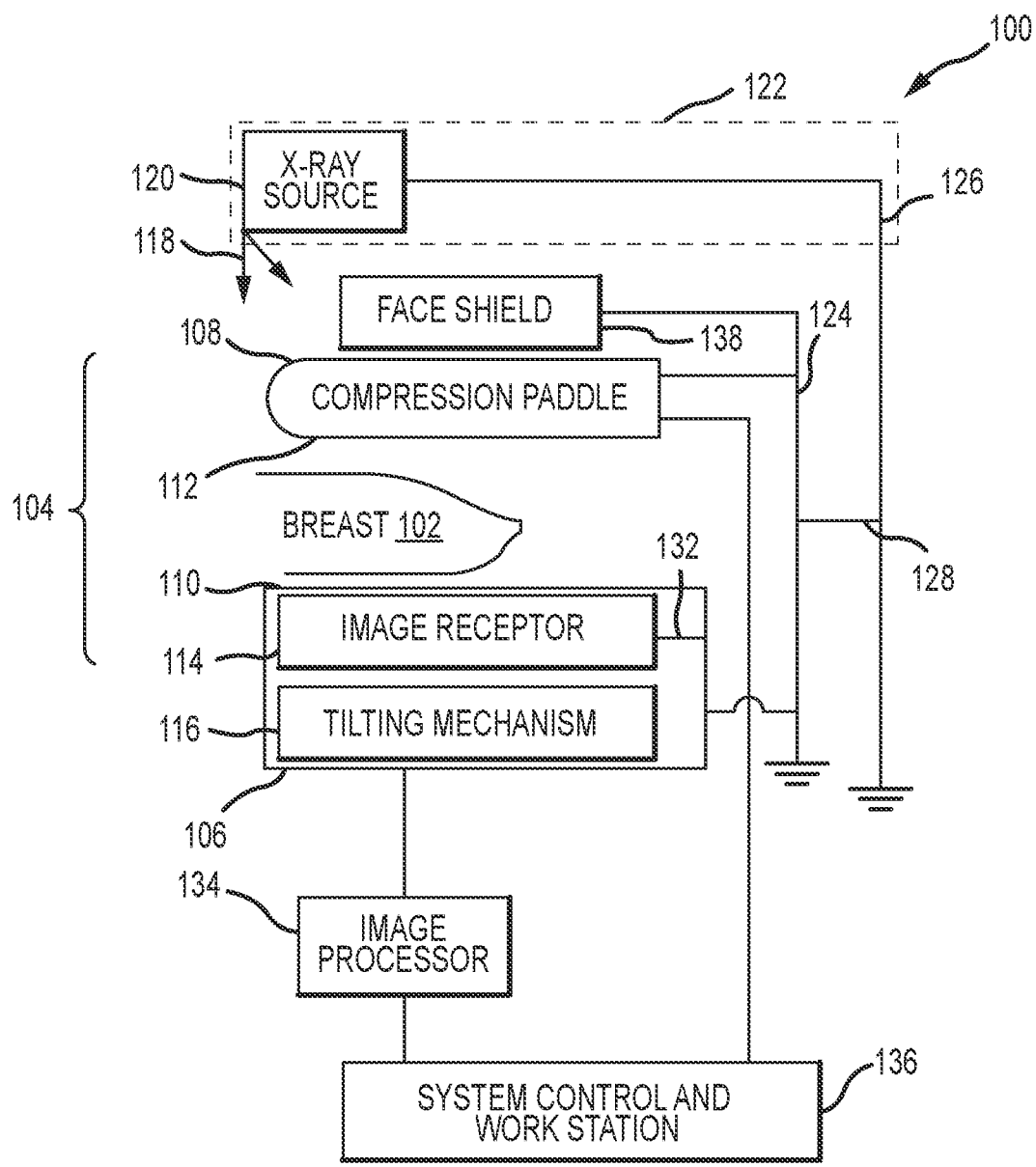
FIG. 1 is a schematic view of an example breast imaging system.

During a breast biopsy procedure, contrast agent may be injected into the patient's bloodstream and contrast-enhanced x-ray imaging of the breast may be performed to locate a site for biopsy and/or facilitate positioning of a biopsy device relative to the site. In some examples, the contrast-enhanced x-ray imaging may be utilized when an area of interest for biopsy (e.g., a lesion) is characterized by abnormal vascularity, and would otherwise be difficult to visualize using standard x-ray imaging. Once the lesion and corresponding site for biopsy is located and the biopsy device positioned, a core sample of breast tissue may be removed from the site as a specimen for diagnostic evaluation. It is then critical to confirm that the specimen includes breast tissue from the intended area of interest for biopsy (e.g., that the specimen includes the lesion) prior to sending the specimen out for the diagnostic evaluation. However, when contrast-enhanced x-ray imaging is performed, traditional specimen imaging systems (e.g., cabinet x-ray systems) that capture a low energy image of the specimen cannot successfully confirm the specimen was removed from the intended area because the contrast agent is translucent to low energy x-rays, as described in greater detail below.

Examples as described herein provide systems and methods for confirming tissue specimens removed using contrast-enhanced x-ray imaging. For example, upon receiving a specimen of breast tissue removed from a site of a patient's breast subsequent to an injection of a vascular contrast agent into the patient, high and low energy images of the specimen are captured and subtracted from one another to generate a subtracted image of the specimen, and based on the subtracted image of the specimen, a determination is made that the contrast agent is present within the specimen to confirm the site from which the specimen was removed is an intended area of interest for biopsy.

Lesions are active growth sites causing increased blood flow to the area, and due to tumor angiogenesis, cancerous lesions take up contrast agent faster and to a greater degree than do normal tissue or benign lesions because of denser capillaries. Additionally, vascular abnormality associated with the lesion (e.g., malformed or incomplete blood vessels) may cause blood to leak from the vessels and the contrast agent carried within the blood to collect around (e.g., surround) the lesion. Therefore, the contrast agent injected into the patient's blood stream may be found in increased concentrations surrounding the lesion. Generally, there is a limited time frame during which the contrast agent remains in the body as the contrast agent flows via the bloodstream to the kidneys, where it is filtered out. Thus, the specimen of the breast tissue needs to be removed from the body within this limited time frame. However, upon removal of the specimen from the body, blood flow stops causing the contrast agent to be effectively captured within the specimen.

When the specimen is imaged, the contrast agent is opaque to high energy x-rays and translucent to low energy x-rays such that, in the subtracted image, everything is subtracted out except the contrast agent. In other words, the contrast agent is present or visible in the subtracted image. Thus, based on the subtracted image of the specimen, a determination can be made that the contrast agent is present within the specimen to confirm the site from which the specimen was removed is an intended area of interest for biopsy.

In some examples, the system for confirming the removed tissue specimens may be a same imaging system (e.g., a breast imaging system) that performs the contrast-enhanced x-ray imaging to locate the site for biopsy and/or facilitate positioning of the biopsy device relative to the site. The breast imaging system may have a specimen imaging modality that enables the capture of both the high and low energy images of the specimen but at lower doses than the high and low energy images captured of the breast given the smaller, thinner size of the specimen as compared to the breast. As one example, the breast imaging system may be similar to the system described in FIGS. 1 and 2, and may also include components or features, such as those described with reference to FIGS. 3 and 4 below, to facilitate the confirmation of tissue specimens removed using contrast-enhanced x-ray imaging.

In other examples, the system for confirming the removed tissue specimens may be a specimen imaging system that is separate from the breast imaging system. For example, the system may be a cabinet x-ray system for imaging tissue specimen. The specimen imaging system may have an imaging modality that enables capture of both a high energy image and a low energy image at low doses, as opposed to the traditional imaging modality of specimen imaging systems limited to the capture of low energy images at low doses. As one example, the specimen imaging system may be similar to the system described with reference to FIGS. 5, 6, and 7 below.

For clarity, systems and methods to confirm tissue specimens removed from the breast are described herein. However, a similar system or method may be used to confirm specimens removed from tissues other than breast tissue using contrast-enhanced x-ray imaging.

In describing examples illustrated in the drawings, specific terminology is employed for the sake of clarity. However, the disclosure of this patent specification is not intended to be limited to the specific terminology so selected and it is to be understood that each specific element includes all technical equivalents that operate in a similar manner.

Figure 2:
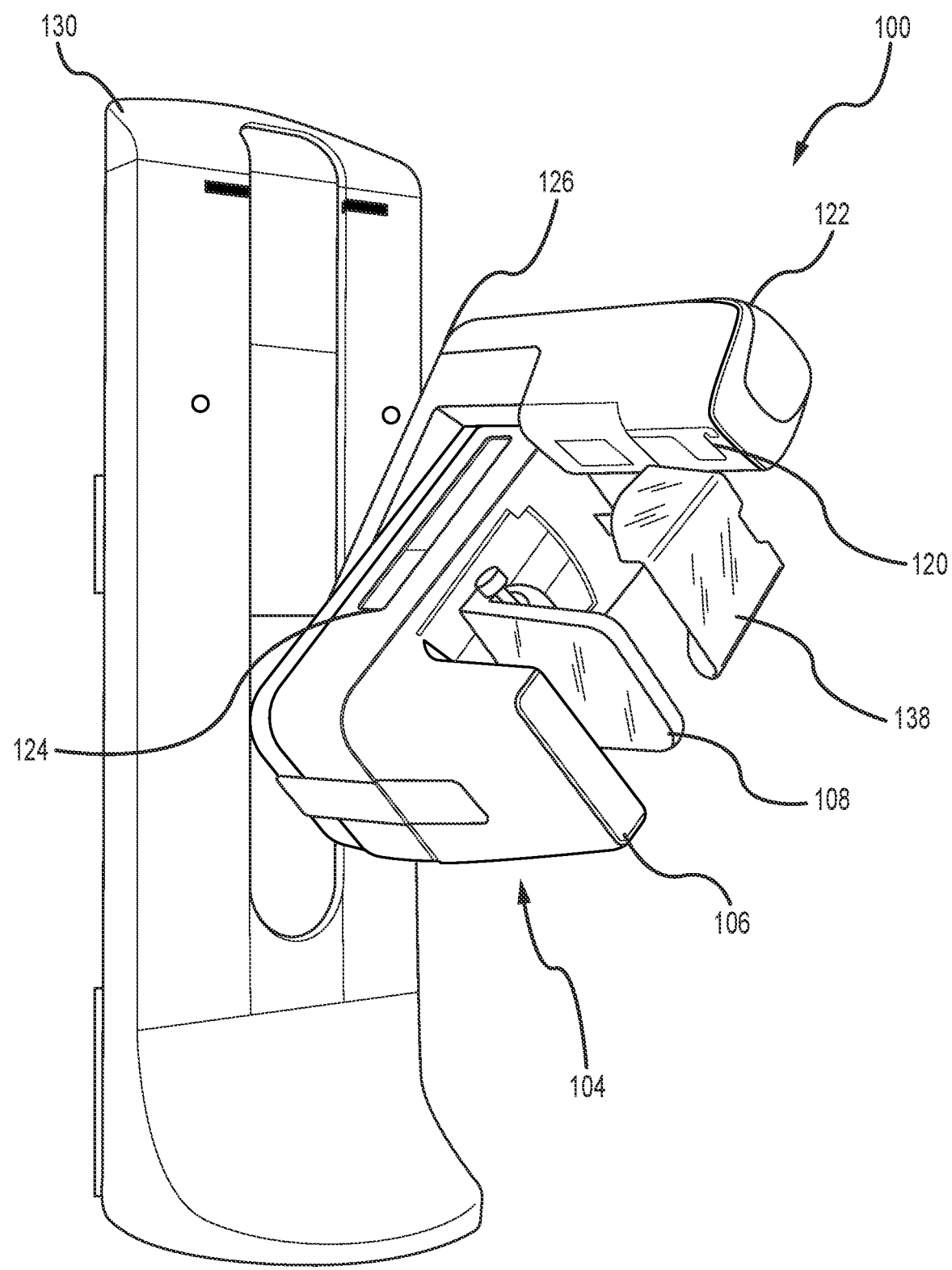
FIG. 2 is a perspective view of the breast imaging system of FIG. 1.

FIG. 1 is a schematic view of an exemplary breast imaging system 100, referred to hereafter as system 100. FIG. 2 is a perspective view of the system 100. Referring concurrently to FIGS. 1 and 2, the system 100 is configured to immobilize a patient's breast 102 for x-ray imaging (either or both of mammography and tomosynthesis) via a breast compression immobilizer unit or compression system 104. In the example, the compression system 104 includes a static breast support platform 106 and a moveable compression paddle 108. The breast support platform 106 and the compression paddle 108 each have a compression surface 110 and 112, respectively, with the compression surface 112 configured to move towards the support platform 106 to compress and immobilize the breast 102. In known systems, the compression surfaces 110, 112 are exposed so as to directly contact the breast 102. The support platform 106 also houses an image receptor 114 (e.g., an x-ray detector) and, optionally, a tilting mechanism 116. The immobilizer unit 104 is in a path of an imaging x-ray beam 118 emanating from an x-ray source 120 disposed within an x-ray tube head 122, such that the beam 118 impinges on the image receptor 114. At least the x-ray source 120 and the image receptor 114 may comprise an image capturing system of the system 100.

The compression system 104 is supported on a first support arm 124 and the x-ray source 120 is supported on a second support arm, also referred to as a tube arm 126. For mammography, support arms 124 and 126 can rotate as a unit about an axis 128 relative to a gantry 130 between different imaging orientations such as cranial-caudal (CC) and mediolateral oblique (MLO) views, so that the system 100 can take a mammogram projection image at each orientation. In operation, the image receptor 114 remains in place relative to the support platform 106 while an image is taken. The immobilizer unit 104 releases the breast 102 for movement of support arms 124, 126 to a different imaging orientation. For tomosynthesis, the support arm 124 stays in place, with the breast 102 immobilized and remaining in place, while at least the tube arm 126 rotates the x-ray source 120 relative to the immobilizer unit 104 and the compressed breast 102 about the axis 128. The system 100 takes plural tomosynthesis projection images of the breast 102 at respective angles of the x-ray beam 118 relative to the breast 102. As such, the compression system 104 and tube arm 126 may be rotated discrete from each other, unless matched rotation is required or desired for an imaging procedure.

Concurrently and optionally, the image receptor 114 may be tilted relative to the breast support platform 106 and coordinated with the rotation of the second support arm 126. The tilting can be through the same angle as the rotation of the x-ray source 120, but may also be through a different angle selected such that the x-ray beam 118 remains substantially in the same position on the image receptor 114 for each of the plural images. The tilting can be about an axis 132, which can but need not be in the image plane of the image receptor 114. The tilting mechanism 116 that is coupled to the image receptor 114 can drive the image receptor 114 in a tilting motion. For tomosynthesis imaging, the breast support platform 106 can be horizontal or can be at an angle to the horizontal, e.g., at an orientation similar to that for conventional MLO imaging in mammography. The system 100 can be solely a mammography system or solely a tomosynthesis system, or a "combo" system that can perform multiple forms of imaging. One example of such a combo system has been offered by the assignee hereof under the trade name Selenia Dimensions.

When the system is operated, the image receptor 114 of the image capturing system produces imaging information in response to illumination by the x-ray beam 118, and supplies it to an image processor 134 for processing and generating x-ray images of the breast 102. A system control and work station unit 136 including software controls the operation of the system and interacts with the operator to receive commands and deliver information including processed x-ray images. In some examples, a face shield 138 may be coupled to the support arm 124 and between the x-ray source 120 and the compression paddle 108. The face shield 138 can be used to prevent the patient from moving into the x-ray beam 118 emitted from the x-ray tube head 122 during imaging.

Additionally or alternatively, a biopsy assembly 139 may be removably coupled to the support arm 124 so as to obtain tissue specimens from the patient's breast 102 when the imaging is being performed as part of a biopsy procedure to locate a site from which the tissue specimen is to be removed and facilitate positioning of the biopsy assembly 139 or components thereof relative to the site.

In some examples, the biopsy procedure may be guided by contrast-enhanced x-ray imaging, particularly if the breast tissue to be removed as a specimen (e.g., a lesion) has vascular abnormalities. Example systems and methods for performing such procedures are described in U.S. Pat. No. 9,020,579, filed on Mar. 8, 2012 and issued on Apr. 28, 2015, and titled SYSTEM AND METHOD FOR DUAL ENERGY AND/OR CONTRAST ENHANCED BREAST IMAGING FOR SCREENING, DIAGNOSIS AND BIOPSY, the disclosure of which is hereby incorporated by reference in its entirety for all purposes.

In one example procedure, such as a contrast-enhanced, dual-energy stereotactic breast tissue biopsy procedure, prior to or after positioning the patient relative to the system 100, an injection of vascular contrast agent may be administered to the patient. The contrast agent may be an iodine-based contrast agent, such as a standard FDA-approved low osmolarity iodine contrast agent. The injection may be administered via the antecubital or forearm vein. Lesions are active growth sites causing increased blood flow to the area, and due to tumor angiogenesis, cancerous lesions take up contrast agent faster and to a greater degree than do normal tissue or benign lesions because of denser capillaries. Additionally, the vascular abnormality associated with the lesion (e.g., malformed or incomplete blood vessels) may cause blood to leak from the vessels and the contrast agent carried within the blood to collect around (e.g., surround) the lesion. Therefore, the contrast agent administered into the patient's blood stream may be found in increased concentrations surrounding the lesion.

Once the contrast agent is administered and a waiting period (e.g., approximately 2 minutes) has passed to allow the contrast agent to concentrate near the lesion, the patient may be positioned relative to system 100 (e.g., if wasn't positioned prior), the breast 102 placed under compression, and the system 100 operated. One or more initial scout images may be captured to identify the lesion and ensure that the lesion is correctly placed in an imaging area shown in FIG. 4 on the compression surface 110 of the breast support platform 106 to be accessed by the biopsy assembly 139. In some examples, the scout images may include a pair of high and low energy images. Alternatively, the scout image may include a standard low energy image.

Subsequently, a stereo pair of images may be captured. For example, when the x-ray source 120 is positioned at a first angle relative to the image receptor 114, the x-ray source 120 may emit x-ray beams 118, including at least a high energy x-ray beam and a low energy x-ray beam, toward the image receptor 114, and the image receptor 114 may produce imaging information in response to illumination by the x-ray beams 118, including a respective high energy image and low energy image for the first angle. The x-ray source 120 may then be re-positioned at a second angle relative to the image receptor 114. The x-ray source 120 may emit x-ray beams 118, including at least a high energy x-ray beam and a low x-ray energy beam, toward the image receptor 114, and the image receptor 114 may produce imaging information in response to illumination by the x-ray beams 118, including a respective high energy image and low energy image for the second angle. The high and low energy images captured for the first and second angle may then be transmitted to an image processor 134 of an image processing system of the system 100.

Once received, the image processor 134 may generate a stereo pair of images from the imaging information provided by the image receptor 114. The stereo pair of images may be subtracted images. For example, the high energy and low energy image captured at the first angle may be subtracted to generate a first subtracted image of the stereo pair of images. The high energy and low energy image captured at the second angle may be subtracted to generate a second subtracted image of the stereo pair of images. The stereo pair of images may then be used to compute a location of the lesion in a coordinate system (e.g., identify target coordinates).

In another example aspect, the target coordinates may be obtained from a contrast-enhanced dual energy tomosynthesis image. The contrast-enhanced dual energy tomosynthesis image may be generated from subtracting image data of a low energy tomosynthesis scan from image data of a high energy tomosynthesis scan. The tomosynthesis scan can be performed as a step and shoot approach where images are acquired when the x-ray tube head 122 is immobile, enabling acquisition of pairs of high energy and low energy images at each angle. Alternatively, the high energy and low energy images can be interleaved during a single continuous tomosynthesis scan (e.g., alternating high energy, low energy, high energy, low energy . . . ) for each angulated position the x-ray tube head 122.

The energies of the high energy and low energy x-ray beams 118 may be dependent on a type of contrast agent injected into the patient and an associated k-edge. As one example, the contrast agent may be an iodine-based contrast agent, where the k-edge of iodine is approximately 33.2 kiloelectronvolts (keV). The high energy x-ray beam 118 may be at energies above the k-edge, while the low energy x-ray beam 118 may at energies below the k-edge. Based on the associated k-edge properties, at high x-ray energies, the contrast agent is opaque, while at low x-ray energies the contrast agent is translucent. Therefore, subtraction of the low energy image from the high energy image captured at the respective angles generates a subtracted image in which only the contrast agent remains (e.g., a contrast-enhanced image). As previously discussed, the contrast agent administered into the patient's blood stream may be found in increased concentrations near (e.g., surrounding) the lesion due to the abnormal vascularity of the lesion, and therefore the contrast agent visible in the subtracted image may define (e.g., visualize) the lesion.

Using the target coordinates, the biopsy assembly 139 may be properly positioned and a biopsy needle, for example, of the biopsy assembly 139 may be inserted into the breast relative to the location of the lesion. Additional images may be captured prior to or during placement of biopsy needle to ensure that the location of the lesion has not moved and/or the biopsy needle has been correctly positioned. Additional details regarding positioning of the biopsy needle and associated imaging techniques are described in U.S. Pat. No. 8,532,745, filed on Feb. 15, 2007 and issued on Sep. 10, 2013, and titled BREAST BIOPSY AND NEEDLE LOCALIZATION USING TOMOSYNTHESIS SYSTEMS, the disclosure of which is hereby incorporated by reference in its entirety for all purposes.

Using the biopsy needle, a core sample of breast tissue may be removed from the location as a specimen. In some examples, once the core sample is removed and while the breast 102 remains under compression, a metallic clip may be placed into the site of the breast 102 from which the tissue was removed. Additional images of the breast 102 may be captured to ensure the metallic clip is placed correctly and can be visualized. The specimen may then be imaged and analyzed to confirm that the core sample was removed from the correct location (e.g., the specimen includes the lesion) before sending the specimen out for diagnostic evaluation.

One challenge when contrast-enhanced x-ray imaging is being implemented by the system 100 is how to efficiently image and analyze the specimen to confirm that the tissue specimens are obtained from the required or desired area of the breast 102 (e.g., to confirm the tissue specimen includes the lesion). For a standard biopsy that does not require contrast-enhanced imaging, the lesion may initially be located based on an identification of clusters of microcalcifications via standard x-ray imaging (e.g., mammography and/or tomosynthesis imaging procedures without contrast enhancement), performed by the system 100, where the microcalcifications are calcium deposits that absorb x-rays causing the microcalcifications to be opaque within the captured x-ray images. Following biopsy, the removed specimen may then be confirmed by identifying a presence of these clusters of microcalcifications within a low energy image of the removed specimen captured by the system 100 or a separate imaging specimen system. However, this traditional specimen confirmation technique is ineffective when confirming tissue specimens obtained under a contrast-enhanced image guided biopsy procedure.

To overcome this challenge, and as described in more detail with reference to FIGS. 3 and 4, the system 100 itself may include a specimen imaging modality that enables dual energy contrast-enhanced imaging of the specimen to confirm or verify the specimen. The system 100 may be similar to imaging system 100 described in U.S. Ser. No. 63/002,898, filed on Mar. 31, 2020, and titled SYSTEMS AND METHODS FOR X-RAY IMAGING TISSUE SPECIMENS, the disclosure of which is hereby incorporated by reference in its entirety for all purposes. The specimen imaging modality may enable emission of low dose, high and low energy x-ray beams to image the specimen.

Additionally or alternatively, and as described in greater detail with reference to FIGS. 5, 6, and 7, a separate specimen imaging system may include a specimen imaging modality that enables dual energy contrast-enhanced imaging of the specimen to confirm or verify the specimen. This specimen imaging system may be similar to imaging system 600 described in U.S. Pat. No. 10,753,836, filed on Feb. 26, 2018 and issued on Aug. 25, 2020, and titled MULTI-AXIS SPECIMEN IMAGING DEVICE WITH EMBEDDED ORIENTATION MARKERS, the disclosure of which is hereby incorporated by reference in its entirety for all purposes. Additionally, the specimen imaging system may include an x-ray source that is capable of emitting low dose, high energy x-rays, whereas traditionally specimen imaging systems are limited to emitting low dose, low energy x-rays.

Generally, in either implementation, the specimen of breast tissue is retained in an apparatus that is positioned relative to an x-ray source and a detector (e.g., of an image capturing system) to enable the image capturing system to capture images of the specimen, including at least a high energy image and a low energy image. The high and low energy x-rays emitted to produce the high and low energy images are dependent on a type of contrast agent injected into the patient and an associated k-edge, where the high energy x-ray is above the k-edge and the low energy x-ray is below the k-edge. The image capturing system, and particularly the detector, is communicatively coupled to an image processing system that receives the high and low energy images, subtracts the low energy image from the high energy image to generate a subtracted image of the specimen, and determines, based on the subtracted image of the specimen, that the contrast agent is present within the specimen to confirm the site from which the specimen was removed is an intended area of interest for the biopsy. For example, based on the associated k-edge properties, at high x-ray energies, the contrast agent is opaque, while at low x-ray energies the contrast agent is translucent. Therefore, the subtraction of the low energy image from the high energy image generates a subtracted image in which only the contrast agent remains. As previously discussed, the contrast agent administered into the patient's blood stream may be found in increased concentrations near (e.g., surrounding) the lesion due to the abnormal vascularity of the lesion, and therefore the contrast agent visible in the subtracted image is indicative of a correct area of tissue being removed.

Of note, there is a limited time frame during which the contrast agent remains in the body as the contrast agent flows via the bloodstream to the kidneys, where it is filtered out. Thus, the specimen of the breast tissue needs to be removed within this limited time frame. However, upon removal of the specimen, blood flow stops causing the contrast agent to be effectively captured within the specimen. It is unlikely that the contrast agent within the specimen will diffuse or otherwise wash out once the specimen is removed from the breast due to the lack of blood flow.

However, if studies later indicate that some diffusion or wash out does occur, such as after a certain period of time or under certain conditions, the imaging of the specimen may be constrained to occur within that time frame or in the absence of those conditions.

Figure 3:
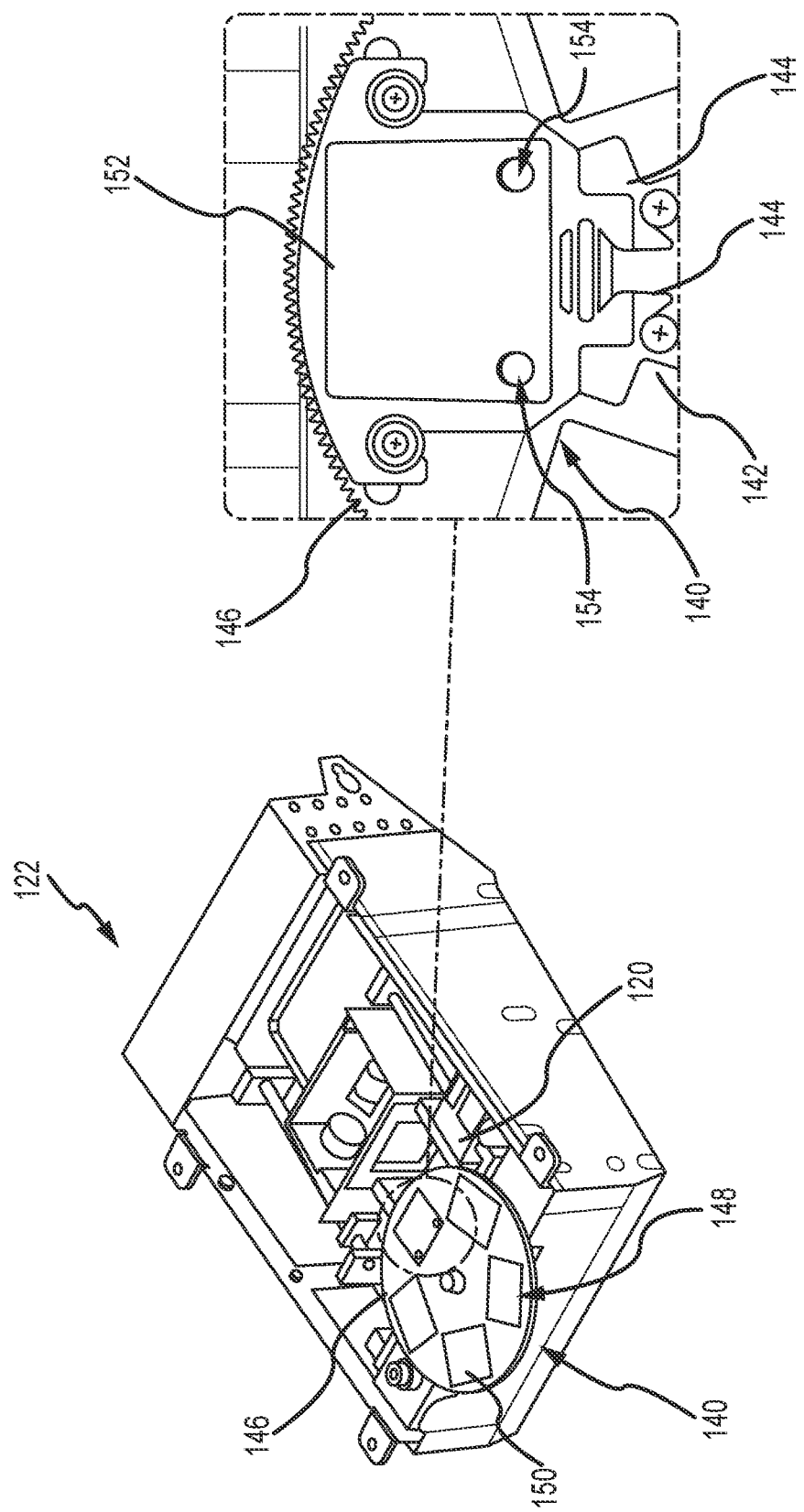
FIG. 3 is an internal perspective view of an x-ray tube head of the breast imaging system shown in FIGS. 1 and 2 that includes a filter wheel assembly disposed therein.
Figure 4:
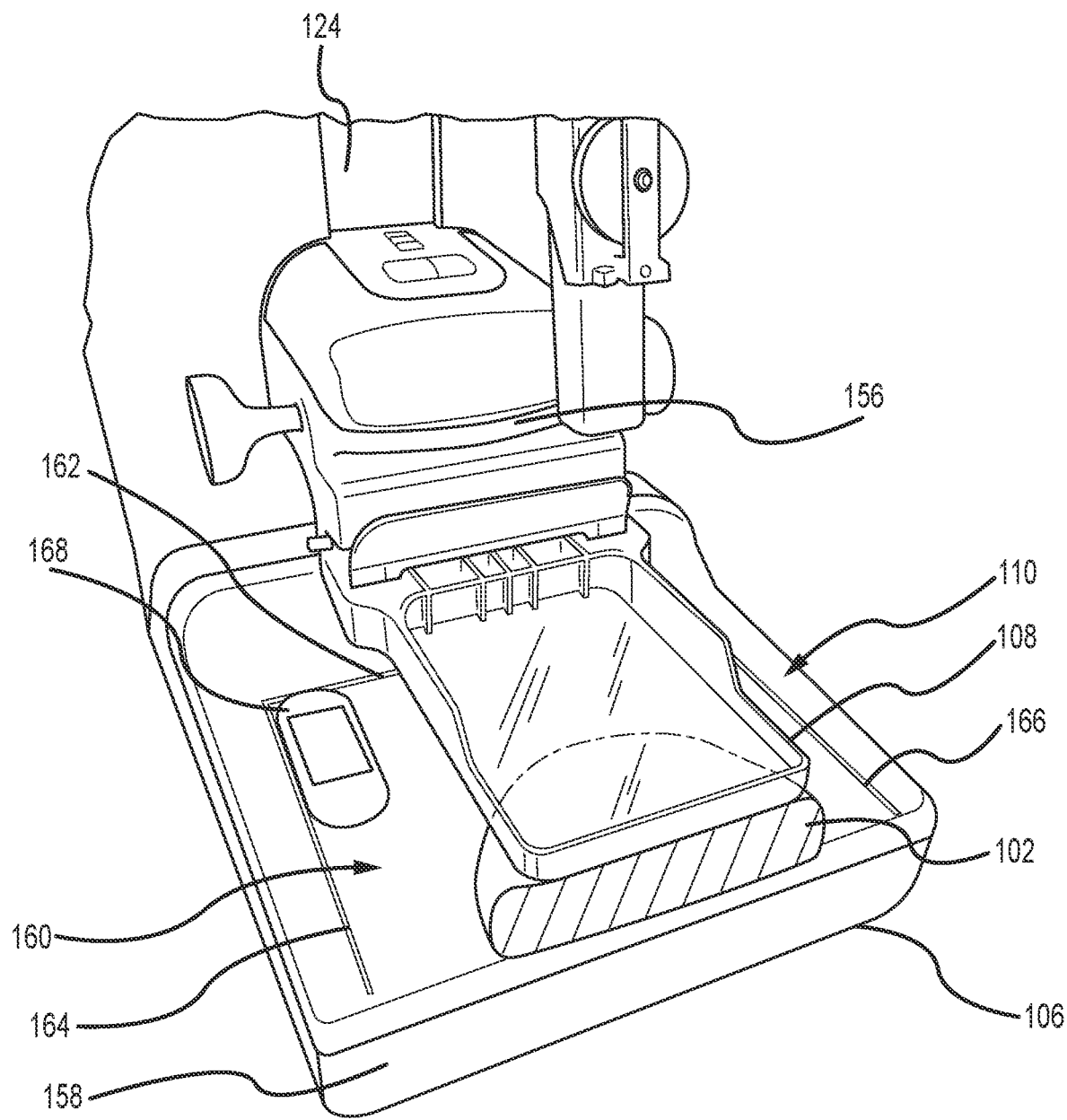
FIG. 4 is a perspective view of a support platform of the breast imaging system shown in FIGS. 1 and 2.

FIGS. 3 and 4 describe additional components or features of the system 100 when the system 100 itself is implemented to confirm tissue specimens. In some examples, the system 100 may have a separate image capturing system for the specimen (e.g., a separate x-ray source and image receptor). For example, the system may include a primary x-ray source and receptor for mammography and tomosynthesis imaging procedures (e.g., x-ray source 120 and image receptor 114) and an additional secondary x-ray source and receptor for tissue specimen imaging procedures. However, this requires a technologist to switch between the two systems. For example, the technologist is required to place the tissue specimen outside of the primary receptor area and into the secondary receptor area, while selectively uncovering the secondary x-ray source in order to perform specimen imaging procedures. Additionally, these secondary imaging systems may increase time spent compressed at the imaging system for the patient because of the need of the technologist to switch between the two separate imaging systems. Further, increased costs may be incurred having duplicate imaging components within the imaging system.

Alternatively, the system 100 may use the same image capturing system (e.g., x-ray source 120 and image receptor 114) for both mammography and tomosynthesis imaging procedures and specimen imaging procedures by implementing one or more filters of the image capturing system, described with reference to FIG. 3.

FIG. 3 is an internal perspective view of the x-ray tube head 122 of the system 100 shown in FIGS. 1 and 2 that includes a filter wheel assembly 140 disposed therein. The x-ray tube head 122 houses the x-ray source 120 that generates the x-ray beam 118 (shown in FIG. 1) for acquiring x-ray images. The x-ray tube head 122 also tilts (e.g., ±relative to the breast support platform 106 (shown in FIG. 2). The x-ray tube head 122 also includes a collimator 142 and the filter wheel assembly 140, both positioned adjacent the x-ray source 120. The collimator 142 includes one or more blades 144 that are configured to move at least partially within the emitted x-ray beam. The blades 144 filter the x-ray beam so that the x-rays that pass through the collimator 142 are aligned in a specific direction. For example, the collimator blades 144 are configured to define a path of the emitted x-ray beam in a direction towards the image receptor 114 (shown in FIG. 1).

The filter wheel assembly 140 includes a filter wheel 146 having a plurality of filter slots 148. Each of the filter slots 148 is configured to receive a filter 150. The filter wheel 146 is rotatable so that the filter slots 148 are selectively positionable within the emitted x-ray beam. The filter wheel assembly 140 is downstream (relative to the emitted x-ray beam direction) from the x-ray source 120 and the collimator 142. The filters 150 can be any filter that enables operation of the system 100 as described herein. For example, one of the filters 150 is a high energy image acquisition filter. The filter 150 can be a copper filter that filters high-energy x-rays for high-energy image acquisitions. Other examples of filters are silver or aluminum filters, or full lead filters so as to enable testing of the imaging system. In another example, the filters 150 are between approximately 2 and 3 thousandth of an inch (mils). In an aspect, the filters 150 are approximately 2.35 mils. As illustrated in FIG. 3, the filter wheel 146 includes five filter slots 148, however, the filter wheel 146 may include any other number of slots 148 as required or desired. For example, the filter wheel 146 may include four filter slots 148.

In the example, a specimen imaging filter 152 is disposed within at least one slot 148 of the filter wheel 146. The specimen imaging filter 152 is configured to enable the x-ray source 120 to capture tissue specimen images as described herein. The specimen imaging filter 152 includes at least one aperture 154 defined therein, and is selectively positionable within the emitted x-ray beam (via the filter wheel 146) so as to block a portion of the emitted x-ray beam and allow the aperture 154 to define a path of the emitted x-ray beam to the image receptor. In an aspect, the specimen imaging filter 152 is formed from lead material so as to block the emitted x-rays except for the aperture 154. In another aspect, the filters 152 is approximately 2.35 mils. In other examples, the specimen imaging filter 152 can be formed from any other material that enables the filter to function as described herein.

The at least one aperture 154 can include a pair of apertures that are sized and shaped to define the path of x-rays to a predetermined focus area on the support platform. In one example, the apertures 154 may be substantially rectangular-shaped. For example, the short edge of the rectangle can be disposed proximate the back of the filter as illustrated, or the long edge of the rectangle can be disposed proximate the back of the filter (not illustrated). In other examples, the apertures 154, may be triangular-shaped, square-shaped, circular-shaped, or any other shape that enables the specimen imaging filter 152 to function as described herein. In the example, the pair of apertures 154 are both disposed at one end of the filter 152 and on opposite left and right sides. This position of the apertures 154 enables the specimen imaging filter 152 to define a path of the emitted x-ray beam that is directed to a right or a left anterior area of the x-ray receptor so as to image tissue specimens with the same x-ray source and receptor that are used for mammography and tomosynthesis images as described above. The collimator blades 144 can be used to selectively cover one of the apertures 154 so that only one aperture 154 (e.g., the left or the right) is used during tissue specimen imaging procedures. The right and left anterior areas are described further below in reference to FIG. 4.

Additionally, the x-ray tube head 122 can tilt (e.g., to the right or the left) during the tissue specimen imaging procedures. For example, to image the right anterior area, the x-ray tube head 122 can tilt to the right. Conversely, to image the left anterior area, the x-ray tube head 122 can tilt to the left. This movement can assist in defining the path of x-rays to the specific area on the support platform and reduce or prevent imaging other components. In another aspect, the x-ray tube head 122 tilts to the opposite side of the collimator blade 144 that covers one of the apertures 154. For example, when the collimator blade 144 covers the left aperture, the x-ray tube head 122 tilts to the right and towards the side of the uncovered right aperture. In an aspect, during the tissue specimen imaging procedures, the x-ray tube head 122 can tilt about ±15° to the left and right. In other aspects, the tilting to the left or right of the x-ray tube head 122 can be less than 15°, or greater than 15°, as required or desired.

In other examples, the at least one aperture 154 can be positioned within the specimen imaging filter 152 to define a path of the emitted x-ray beam that is directed towards specific locations on the support platform surface (e.g., left edge, right edge, or anterior location). In a further example, specimen imaging filter 152 can define a path of the emitted x-ray beam that is directed towards specific locations on the compression paddle (e.g., left edge, right edge, or anterior location). In yet a further example, the at least one aperture 154 can be positioned within the specimen imaging filter 152 to define a path of the emitted x-ray beam that is directed to a specific location of a specimen container that is removably coupleable to the system 100 and independently rotatable relative to the x-ray source 120. In a yet further example, the at least one aperture 154 can be positioned within the specimen imaging filter 152 to define a path of the emitted x-ray beam that is directed to a specific location of a vacuum assisted biopsy device. These additional examples are described in full detail in U.S. Ser. No. 63/002,898.

In the example, the specimen imaging filter 152 can be used with any focal spot size generated by the x-ray source 120. This enables for the tissue specimen to be imaged in any amount of detail as required or desired. For example, using a focal spot size for verification procedures (e.g., a larger focal spot size) or for verification and diagnostic procedures (e.g., a smaller focal spot size).

FIG. 4 is a perspective view of a support platform 106 of the system 100 shown in FIGS. 1 and 2. As described above, the support platform 106 extends from the support arm 124 that also supports the compression paddle 108. The support platform 106 houses the image receptor 114 (shown in FIG. 1) that enables x-ray images to be acquired. The compression surface 110 of the support platform 106 is used to compress the patient's breast 102 (represented in FIG. 4 by a breast phantom) with the compression paddle 108. The compression paddle 108 is coupled to the support arm 124 with a paddle bracket 156 that is configured to move (e.g., in an up and down direction) relative to the support platform 106 and along the support arm 124.

In operation, the patient's breast 102 is compressed between the support platform 106 and compression paddle 108 while one or more imaging procedures are performed on the breast 102 prior to or in conjunction with a biopsy procedure to obtain one or more tissue specimens from the patient's breast 102. The patient's chest wall is typically positioned against a front wall 158 of the support platform 106 to enable breast compression. These images are acquired via the image receptor 114 that is disposed within the platform 106. In the example, the image receptor 114 at least partially defines an imaging area 160 (e.g., the relative size of the receptor) that enables the patient's breast 102 to be imaged. Because the x-ray receptor is below the compression surface 110, the imaging area 160 can be visually identified for the technologist by a box on the compression surface 110. In other examples, the imaging area 160 can be identified by any other indicator(s) as required or desired. For example, the imaging area 160 can be identified by pixel markers on the image receptor 114. The imaging area 160 extends from the front wall 158 of the support platform 106 towards an anterior portion 162 of the compression surface 110 that is proximate the support arm 124. Additionally, the imaging area 160 includes left and right portions 164, 166, respectively.

Once tissue specimens are removed during the biopsy procedure, the tissue specimens can then be imaged by the system 100. The tissue specimen imaging can be for confirmation (e.g., to verify that the area of interest including the lesion was biopsied), diagnostics, and/or any other procedure as required or desired. In some examples, the patient's breast may remain under compression while the tissue specimen is being imaged such that additional tissue of interest may be located and obtained more quickly (e.g., before the contrast agent washes out) if the specimen is not confirmed or verified as including the lesion. As previously discussed, in order to increase the efficiency of the tissue specimen imaging process and to decrease patient discomfort (e.g., from long time periods of breast compression), the same image capturing system (e.g., the x-ray source 120 and image receptor 114) of the system 100 for breast imaging may be used for specimen imaging.

In the example, after biopsy, the technologist can place the tissue specimens in an apparatus for retaining the tissue specimen, where the apparatus may be placed relative to the x-ray source 120 and image receptor 114 to enable the image capturing system to capture images of the specimen. In one example, the apparatus may be a specimen container 168 as shown in FIG. 4. The specimen container 168 can be a radiolucent container that is configured to retain tissue specimens and enable the tissue specimens to be moved by the technologist. In an aspect, the specimen container 168 is configured to be positioned within the imaging area 160 and lay flat on the support platform 106. In some examples, the specimen container 168 may be disposable, for example, such as those produced by Faxitron Bioptics. Additionally or alternatively, the specimen container 168 can hold a plurality of tissue specimens; for example, at least four to six separate specimens. The plurality of tissue specimens can be separated into discrete compartments within the specimen container 168 or all within a single large compartment.

As illustrated in FIG. 4, the size and shape of the specimen container 168 allows for the container to be placed within the imaging area 160 and offset from the compression paddle 108 so that the patient's breast 102 can remain compressed during tissue specimen imaging. For example, the specimen container 168 can be placed in a left anterior area (e.g., towards the corner of the anterior portion 162 and the left portion 164) and/or a right anterior area (e.g., towards the corner of the anterior portion 162 and the right portion 166). In an aspect, pixel markers can be used for the placement of the specimen container 168. For example, markers for pixel location can be placed on rear anterior line and edges on each sides (e.g., 0 pixel line). This offset positioning relative to a centerline of the image receptor 114 also corresponds with the structure (e.g., the apertures) of the specimen imaging filter 152 described above in reference to FIG. 3 so that the path of the x-ray beam is directed to the tissue specimens retained within the specimen container 168 and positioned within the imaging area 160. Furthermore, this process for tissue specimen imaging is performed within the imaging area 160 of the image receptor 114 and duplicate imaging components are not needed. In some examples, the focal spot size of the x-ray source 120 can be adjusted as required for verification or diagnostic imagining. Additionally, the x-ray tube head can tilt towards the left or right imaging area as required or desired.

The specimen container 168 is one non-limiting example of an apparatus for retaining the specimen. In other examples, not illustrated herein, the specimen may be placed in a container that replaces the compression paddle or placed directly on the compression paddle at various locations (e.g., a left edge, a right edge, or an anterior location). In further examples, the specimen may be placed in a specimen container that is removably coupleable to the breast imaging system and independently rotatable relative to the x-ray source. In yet further examples, the biopsy assembly 139 may include a vacuum assisted biopsy device comprising a reservoir that captures removed tissue specimen and is then used for tissue specimen imaging. For example, the reservoir can moved (e.g., up and/or down relative to the x-ray source, and/or rotate) to facilitate tissue specimen imaging procedures. These additional examples are described in full detail in U.S. Ser. No. 63/002,898.

The example system 100 illustrated and described with reference to FIGS. 1-4 is a non-limiting, non-exclusive example of a breast imaging system comprising a specimen imaging modality that enables confirmation of tissue specimens removed using contrast-enhanced biopsy. Other breast imaging systems having one or more x-ray sources capable of emitting low dose, high energy and low energy x-rays may be similarly implemented to generate subtracted images from the high and low energy images for use in confirmation.

In other aspects, the tissue specimens removed using contrast-enhanced x-ray imaging (e.g., during a contrast-enhanced, dual-energy stereotactic breast tissue biopsy procedure, among other similar procedures) may be confirmed using a specimen imaging system separate from the system used for breast imaging during the procedure (e.g., separate from system 100).

Figure 5:
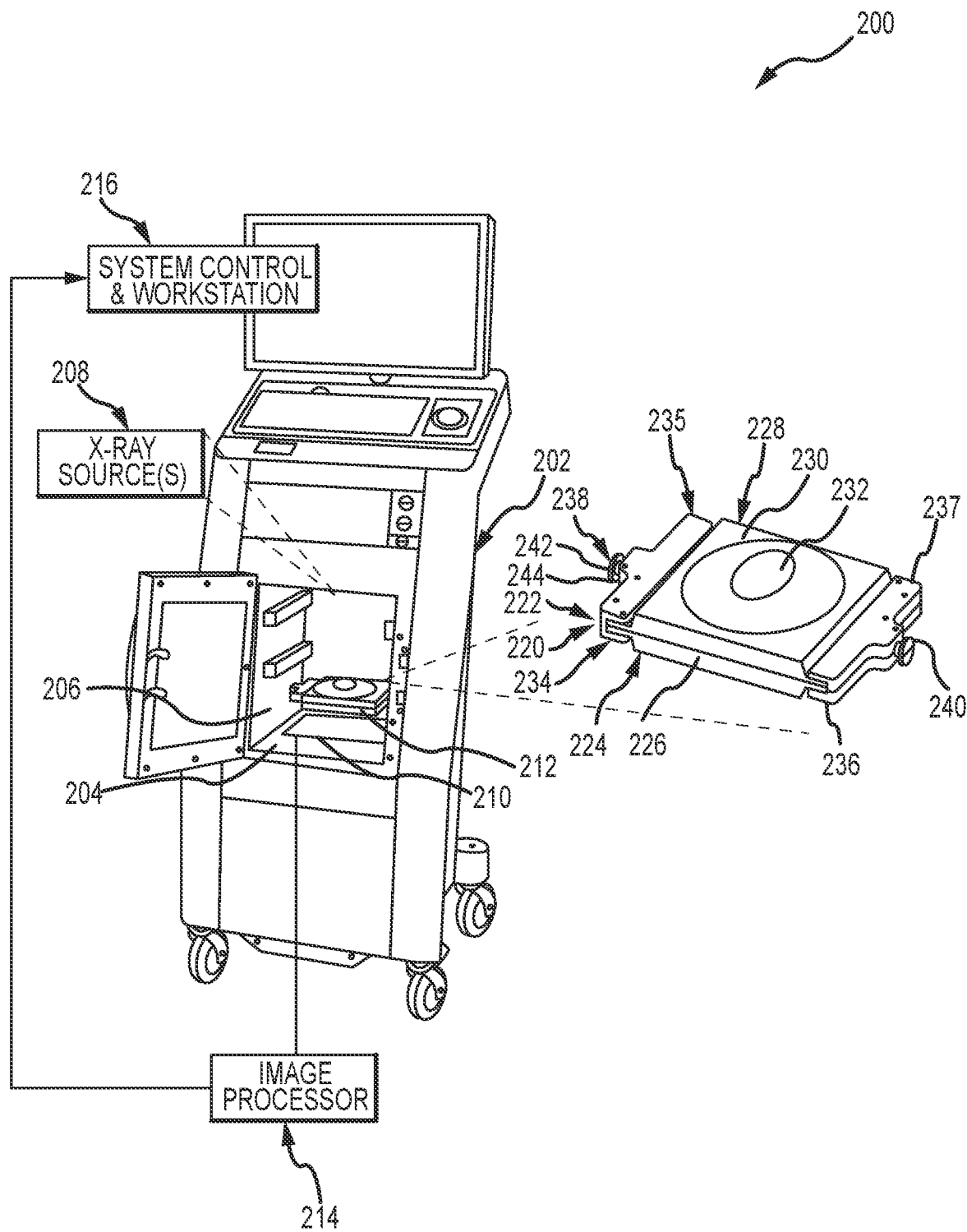
FIG. 5 is a perspective view of an example specimen imaging system including an imaging chamber and an apparatus positioned within the imaging chamber.

FIG. 5 is a perspective view of an example specimen imaging system 200, referred to hereafter as system 200, including an imaging chamber 204 and an apparatus 212 positioned within the imaging chamber 204. FIG. 6 is a perspective view of the system 200 shown in FIG. 5 when the apparatus 212 is positioned in a first orientation within the imaging chamber 204. FIG. 7 is a perspective view of the system 200 shown in FIG. 5 when the apparatus 212 is positioned in a second orientation within the imaging chamber 204. The system 200 is similar to the imaging system 600 described in U.S. Pat. No. 10,753,836. The system 200 may also include an imaging modality that enables both high and low energy x-rays to be emitted at low doses to image the specimen (e.g., rather than just low dose, low energy x-rays) in order to confirm tissue specimens removed using contrast-enhanced x-ray imaging.

Figure 6:
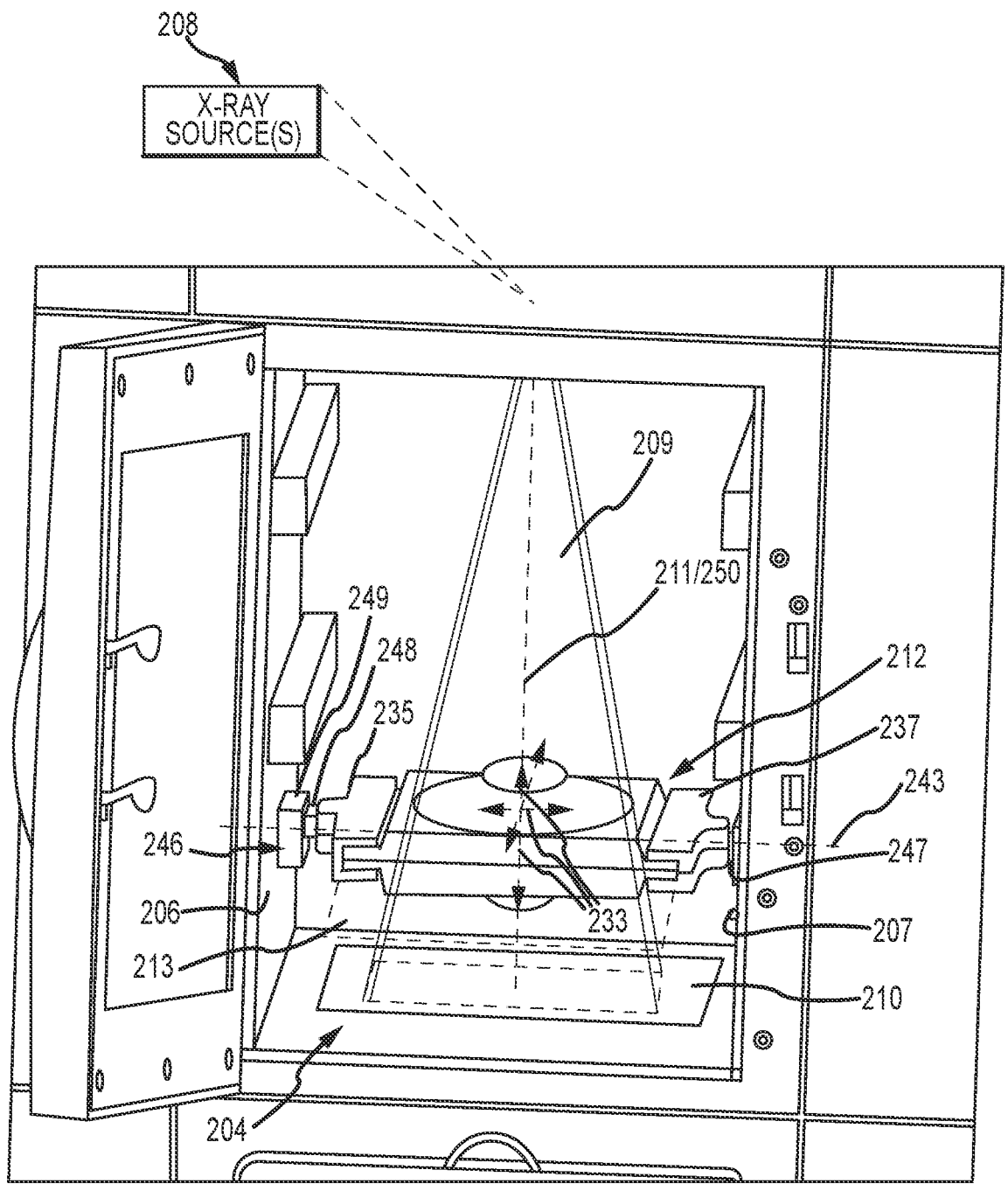
FIG. 6 is a perspective view of the specimen imaging system shown in FIG. 5 when the apparatus is positioned in a first orientation within the imaging chamber.
Figure 7:
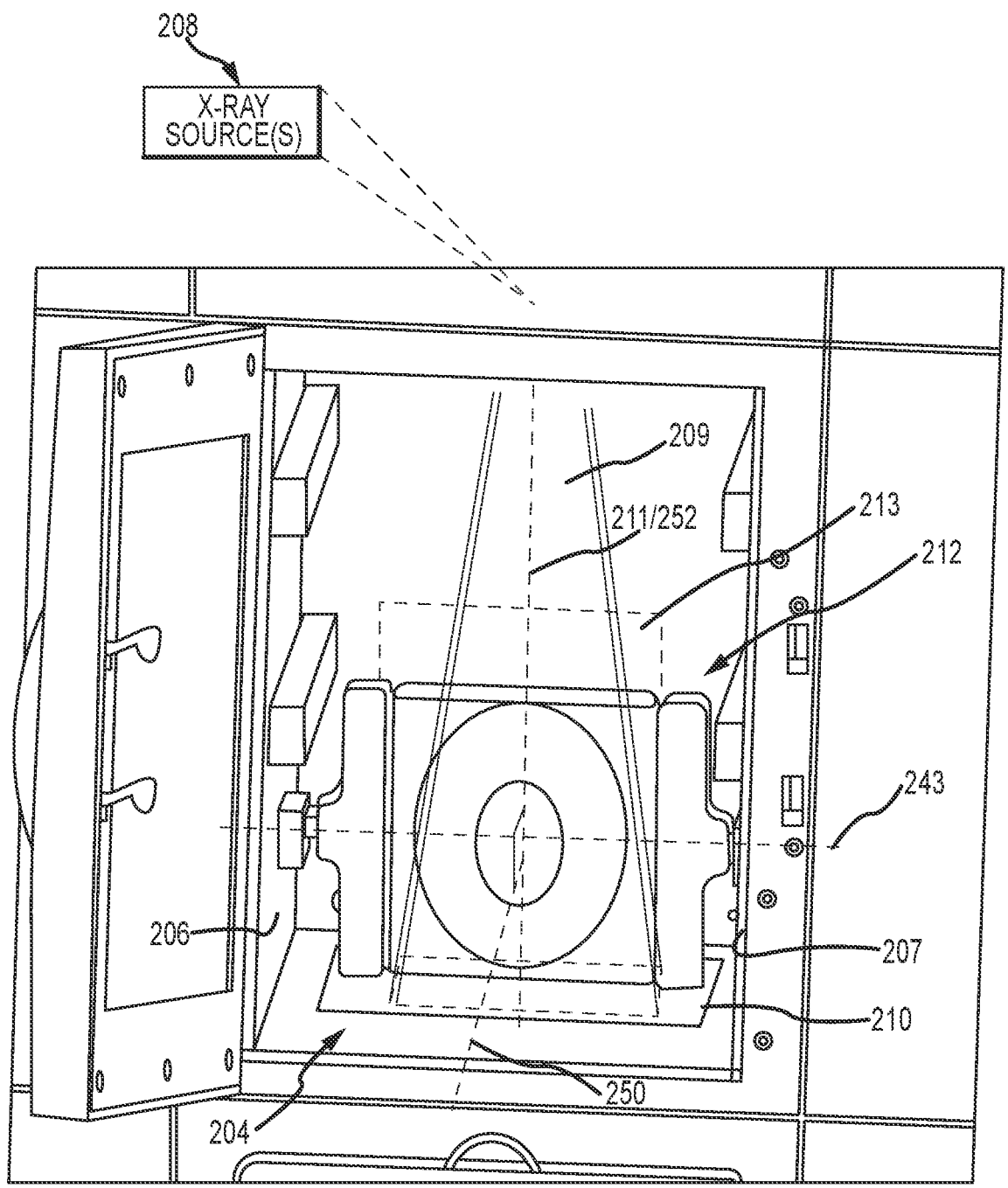
FIG. 7 is a perspective view of the specimen imaging system shown in FIG. 5 when the apparatus is positioned in a second orientation within the imaging chamber.

Referring concurrently to FIGS. 5, 6, and 7, the system 200 may broadly include a housing 202 that includes the imaging chamber 204. The imaging chamber 204 may be defined by opposite sidewalls 206, 207 or support surfaces, one or more x-ray source(s) 208 disposed adjacent to one end of the imaging chamber 204 (e.g., adjacent a top of the imaging chamber 204), and a detector 210 disposed adjacent an opposite end of the imaging chamber 204 (e.g., adjacent a bottom of the imaging chamber 204). At least the x-ray sources 208 and the detector 210 may comprise an image capturing system of the system 200. The apparatus 212 retains a specimen 232 for imaging, and the apparatus 212 may be positioned within the imaging chamber 204 relative to the x-ray source(s) 208 and the detector 210. In some examples, the specimen 232 may be a core sample of tissue removed from a breast using contrast-enhanced x-ray imaging, and thus contrast agent injected into the patient's blood stream prior to biopsy may be captured within the specimen (e.g., surrounding a lesion) upon removal.

The x-ray source(s) 208 may be configured to emit low dose x-ray beams 209 of varying energies along an imaging axis 211 through the imaging chamber 204, including through the apparatus 212 retaining the specimen 232, towards the detector 210. In some examples, the system 200 includes at least two x-ray sources 208, where a first x-ray source is capable of emitting low dose, high energy x-rays and a second x-ray source is capable of emitting low dose, low energy x-rays. In other examples, the x-ray source 208 may be a single x-ray source 208 capable of emitting both low dose, high and low energy x-rays via implementation of one or more filters (e.g., a high energy acquisition filter to enable capture of the high energy images). The energies of the high energy and low energy x-rays may be dependent on a type of contrast agent injected into the patient and an associated k-edge. The high energy x-ray may be at energies above the k-edge, while the low energy x-rays may at energies below the k-edge.

When the system 200 is operated, the detector 210 produces imaging information in response to illumination by the x-ray beams, and supplies it to an image processor 214 of an image processing system of the system 200. The image processor 214 processes and generates x-ray images, including subtracted images, of the specimen 232. For example, the image processor 214 may receive at least the high energy image and the low energy image of the specimen 232, subtract the low energy image from the high energy image to generate a subtracted image of the specimen 232, and determine, based on the subtracted image, a presence of the contrast agent in the specimen 232 to confirm the site from which the specimen was removed is an intended area of interest for biopsy. For example, based on the associated k-edge properties, at high x-ray energies, the contrast agent is opaque, while at low x-ray energies the contrast agent is translucent. Therefore, the subtraction of the low energy image from the high energy image generates a subtracted image in which only the contrast agent remains. As previously discussed, the contrast agent administered into the patient's blood stream may be found in increased concentrations near (e.g., surrounding) the lesion due to the abnormal vascularity of the lesion, and therefore the contrast agent visible in the subtracted image is indicative of a correct area of tissue being removed.

A system control and work station unit 216 including software controls the operation of the system 200 and interacts with the operator to receive commands and deliver information including the processed x-ray images of the specimen (e.g., the subtracted image of the specimen).

The apparatus 212 may include a first positioning member 220 and a second positioning member 222. The first positioning member 220 may include a body 224 and an at least partially elastically deformable portion 226 (e.g., a "retention" portion or member). Similarly, the second positioning member 222 may include a body 228 and an at least partially elastically deformable portion 230 (e.g., a "retention" portion or member). Upon removal from the breast and prior to imaging, the specimen 232 may be placed over the elastically deformable portion 226 of the first positioning member 220, and the second positioning member 222 may be secured to the first positioning member 220 (e.g., in a non-movable, fixed manner), causing the elastically deformable portions 226, 230 of the first and second positioning members 220, 222 to elastically deform about opposite portions of the specimen 232 to thereby retain the specimen 232 therebetween within a specimen support volume 233 of the apparatus 212 for use in accurate imaging of the specimen.

As shown, the body 224 of the first positioning member 220 may include first and second support ledges 234, 236 over which opposite ends of the elastically deformable portion 226 are configured to be appropriately secured (e.g., via adhesives, bonding, or the like). Similarly, the body 228 of the second positioning member 222 includes first and second support ledges 235, 237 over which opposite ends of the elastically deformable portion 230 are configured to be appropriately secured (e.g., via adhesives, bonding, or the like). The support ledges 234, 236 and 235, 237 may extend laterally away from the opposite ends of the elastically deformable portions 226, 230. Furthermore, the apparatus 212 includes one or more features that allow for fixable positioning of the first and second positioning members 220, 222 to allow for substantial non-movable retaining of the specimen 232 between the elastically deformable portions 226, 230 as well as suspension of the specimen 232 within the apparatus 212.

Each of the elastically deformable portions 226, 230 of the first and second positioning members 220, 222 is configured to at least partially transmit an x-ray beam therethrough to allow for imaging of the specimen 232 along first and second orthogonal axes 250, 252 through the apparatus 212 (e.g., including through the specimen support volume 233) to obtain respective first and second sets of images of the specimen (e.g., for use in specimen confirmation). Additionally, each of the elastically deformable portions 226, 230 is configured to at least partially elastically deform about an opposite portion of a specimen 232 to retain the specimen within the apparatus 212 when the first and second positioning members 220, 222 are secured to each other.

In one arrangement, each of the elastically deformable portions 226, 230 may be constructed of a sheet, layer, etc. of any appropriate radiolucent solid (e.g., polymeric) foam (s), film (e.g., polyurethane, etc.), or combination thereof. The material properties (e.g., compression resistance, modulus of elasticity, etc.) and/or dimensions (e.g., thickness) of the elastically deformable portions 226, 230 of the first and second positioning members 220, 222 may be selected to retain the specimen 232 within the specimen support volume 233 of the apparatus 212 against movement relative to the apparatus 212. Additionally, the material properties and/or dimensions of the elastically deformable portions 226, 230 may be selected or configured to substantially inhibit deformation of the specimen 232 from its natural shape and dimensions while still retaining the specimen 232 against movement relative to the apparatus 212.

In some examples, orthogonal imaging of the specimen 232 to obtain first and second orthogonal images may be important in relation to analyzing and confirming the specimen was removed from the intended area of interest for biopsy. After the specimen 232 has been placed between the elastically deformable portions 226, 230 and the first and second positioning members 220, 222 have been positioned so as to elastically deform the elastically deformable portions 226, 230 about opposite portions of the specimen 232 as illustrated, the apparatus 212 may be placed into imaging chamber 204. As shown in FIG. 6, the apparatus 212 may first be placed so that the x-ray sources 208 transmit high energy and low energy x-ray beams 209 through the specimen support volume 233 along the first of the two orthogonal axes (e.g., first axis 250). The first axis 250 is substantially coincident with or parallel to the imaging axis 211, and is substantially perpendicular to a reference plane 213 disposed between the elastically deformable portions 226, 230. In some examples, the apparatus 212 may then be repositioned. As shown in FIG. 7, the apparatus 212 may be rotated about a rotation axis 243 by 90° (e.g., where the rotation axis 243 is substantially perpendicular to the imaging axis 211) so that the x-ray sources 208 transmit high energy and low energy x-ray beams 209 through the specimen support volume 233 along the second of the two orthogonal axes (e.g. second axis 252) to generate a second set of high and low energy images. The second axis 252 is substantially coincident with or parallel to the imaging axis 211 and to the reference plane 213.

In some examples, the apparatus 212 may be placed directly on the detector 210. However, in other examples, to facilitate the orthogonal reorientation or positioning of the apparatus 212, the apparatus 212 may be suspended within the imaging chamber 204. For example, the opposite ends of the apparatus 212 may be respectively interconnected (e.g., removably interconnected) to the first and second sidewalls 206, 207 of the imaging chamber 204 to at least partially space the apparatus 212 from the x-ray source(s) 208 and the detector 210 and thereby facilitate orthogonal reorientation of the apparatus 212 (e.g., where a first orientation is shown in FIG. 6 and a second orientation is shown in FIG. 7). As an example, the apparatus 212 may include opposite first and second connection components 238, 240 that are respectively configured to engage with complimentary first and second connection components 246, 247 on the first and second sidewalls 206, 207 of the imaging chamber 204. For instance, the first and second connection components 238, 240 may be in the form of fasteners having a shaft 242 (e.g., that defines the rotation axis 243 of the apparatus 212) and a head 244 attached to the shaft 242. In one embodiment, each of the first and second positioning members 220, 222 may include a portion (e.g., a half) of each of the first and second connection components 238, 240, whereby a complete or full first and second connection component 238, 240 is automatically formed upon interconnection of the first and second positioning members 220, 222.

The first and second connection components 246, 247 on the first and second sidewalls 206, 207 may, in one example, be in the form of openings, recesses or hubs that are configured to respectively receive the first and second connection components 238, 240 of the apparatus 212. For instance, each of the first and second connection components 246, 247 on the first and second sidewalls 206, 207 may include a slot 248 for slidable and rotatable receipt of the shaft 242 and a channel 249 for slideable and rotatable receipt of the head 244. In this regard, the first and second connection components 238, 240 of the apparatus 212 may be respectively engaged with (e.g., inserted or clipped into) the first and second connection components 246, 247 on the first and second sidewalls 206, 207 of the imaging chamber 204 so that the first axis 250 disposed through the specimen support volume 233 is substantially coincident with or parallel to the imaging axis 211, as shown in FIG. 6. The x-ray sources 208 may generate and transmit a high energy x-ray beam 209 and a low energy x-ray beam along imaging axis 211 and the first axis 250 through the apparatus 212, specimen 232, and specimen support volume 233 for receipt at the detector 210 to generate a first set of high energy and low energy images of the specimen 232.

After the first set of high and low energy images of the specimen 232 has been obtained in the position shown in FIG. 6, the apparatus 212 may optionally be reoriented as described above and as shown in FIG. 7. The specimen 232 may then be imaged to obtain a second set of high and low energy images of the specimen 232. The first and second set of images may be provided to the image processor 214. For each set, the low energy image may be subtracted from the high energy image to generate a subtracted image. The subtracted image from one or both of the sets may then be analyzed by the image processor 214 to identify a presence of the contrast agent and confirm the specimen was removed from the correct area of breast tissue (e.g., includes the lesion).

The example system 200 illustrated and described with reference to FIGS. 5-7 is a non-limiting, non-exclusive example of a specimen imaging system that may include an imaging modality enabling confirmation of tissue specimens removed using contrast-enhanced biopsy. Other specimen imaging systems having one or more x-ray sources capable of emitting low dose, high energy and low energy x-rays may be similarly implemented to generate subtracted images from the high and low energy images for use in confirmation.

Figure 8:
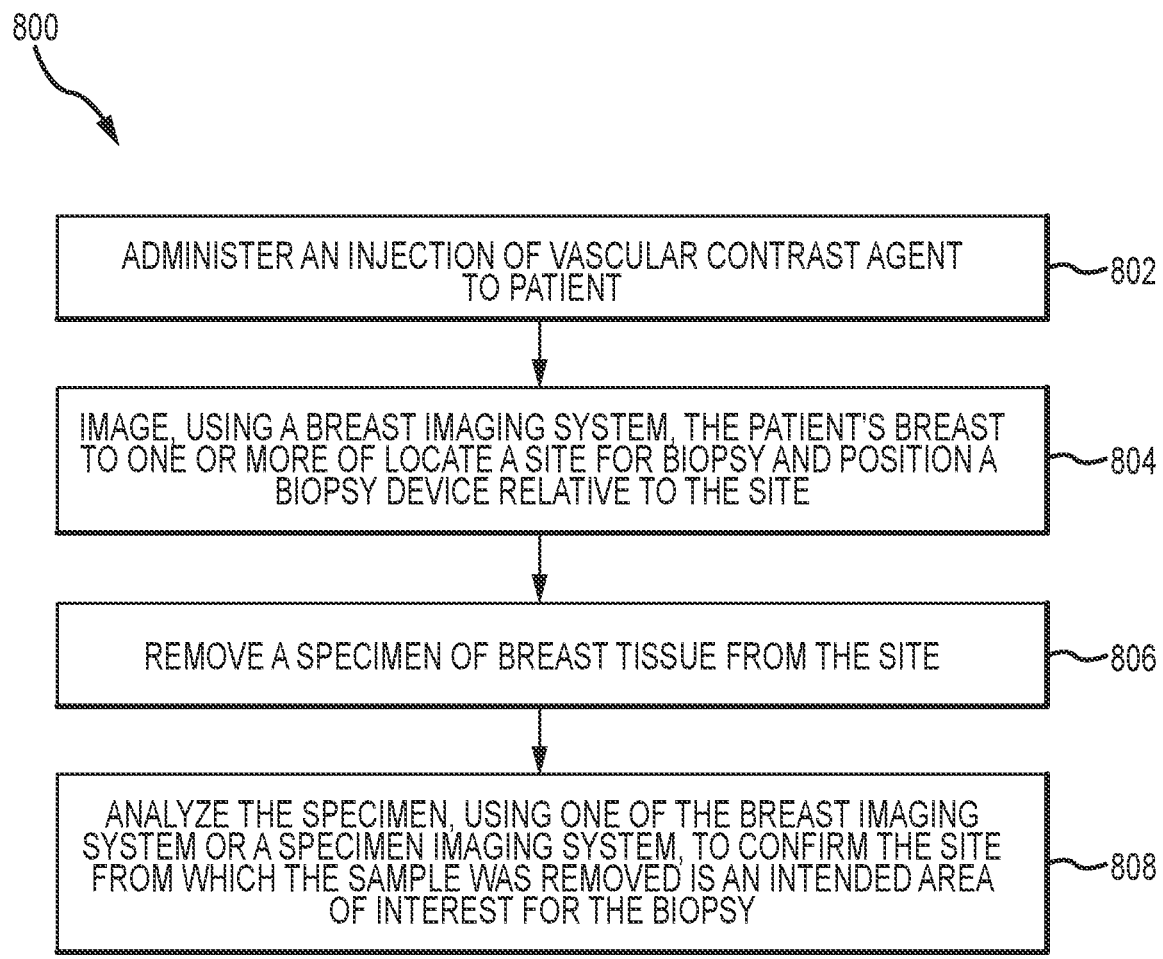
FIG. 8 is an example method for using contrast-enhanced x-ray imaging to facilitate a biopsy.

FIG. 8 is an example method 800 for using contrast-enhanced x-ray imaging to facilitate biopsy and subsequently confirm a tissue specimen removed. The method 800 includes operations 802, 804, 806, and 808, and is representative of an example clinical scenario in which the technology described herein is implemented.

A patient may be brought into a room in which the biopsy will be performed and seated for their comfort. At operation 802, an injection of vascular contrast agent may be administered to the patient. In some examples, the contrast agent may be an iodine-based contrast agent, such as a standard FDA-approved low osmolarity Iodine contrast agent. The injection may be administered via the antecubital or forearm vein. Lesions, particularly cancerous lesions, are active growth sites causing increased blood flow to the area, and due to tumor angiogenesis, cancerous lesions take up contrast agent faster and to a greater degree than do normal tissue or benign lesions because of denser capillaries. Additionally, the vascular abnormality associated with the lesion (e.g., malformed or incomplete blood vessels) may cause blood to leak from the vessels and the contrast agent carried within the blood to collect around (e.g., surround) the lesion. Therefore, the contrast agent administered into the patient's blood stream may be found in increased concentrations surrounding the lesion.

Once the contrast agent is administered and a waiting period (e.g., approximately 2 minutes) has passed to allow the contrast agent to concentrate near the lesion, the patient is positioned relative to a breast imaging system (e.g., system 100), the patient's breast is placed under compression, and the patient's breast may then be imaged at operation 804 to locate a site for biopsy (e.g., an area of tissue including the lesion) and/or facilitate position of a biopsy device relative to the site, as described in detail with reference to FIG. 1.

Using the biopsy needle, a core sample of breast tissue may be removed from the site as a specimen at operation 806. When the specimen is removed from the body, blood flow stops causing the contrast agent that was administered to the patient at operation 802 and collected around the lesion to be effectively captured within the specimen (e.g., if the lesion was included in the core sample of breast tissue removed as the specimen). Once removed, the specimen may be placed in an apparatus operable to retain the specimen. The apparatus that receives and retains the specimen may be dependent on which type of system is being used to confirm the specimen, described with greater detail with reference to operation 806.

At operation 806, the specimen may be analyzed to confirm the site from which the sample was removed is an intended area of interest for the biopsy (e.g., the specimen includes the lesion). Once confirmed, the specimen may be sent off for diagnostic evaluation (e.g., to determine whether the lesion is malignant or benign). In some examples, the analysis may be performed by the same imaging system that performed that imaging of the breast in operation 804 (e.g., a breast imaging system). In other examples, the analysis may be performed by a specimen imaging system separate from the breast imaging system. As described in detail with reference to FIG. 9, the confirmation analysis involves dual energy, contrast-enhanced x-ray imaging of the specimen to detect a presence of the contrast agent within the specimen.

Figure 9:
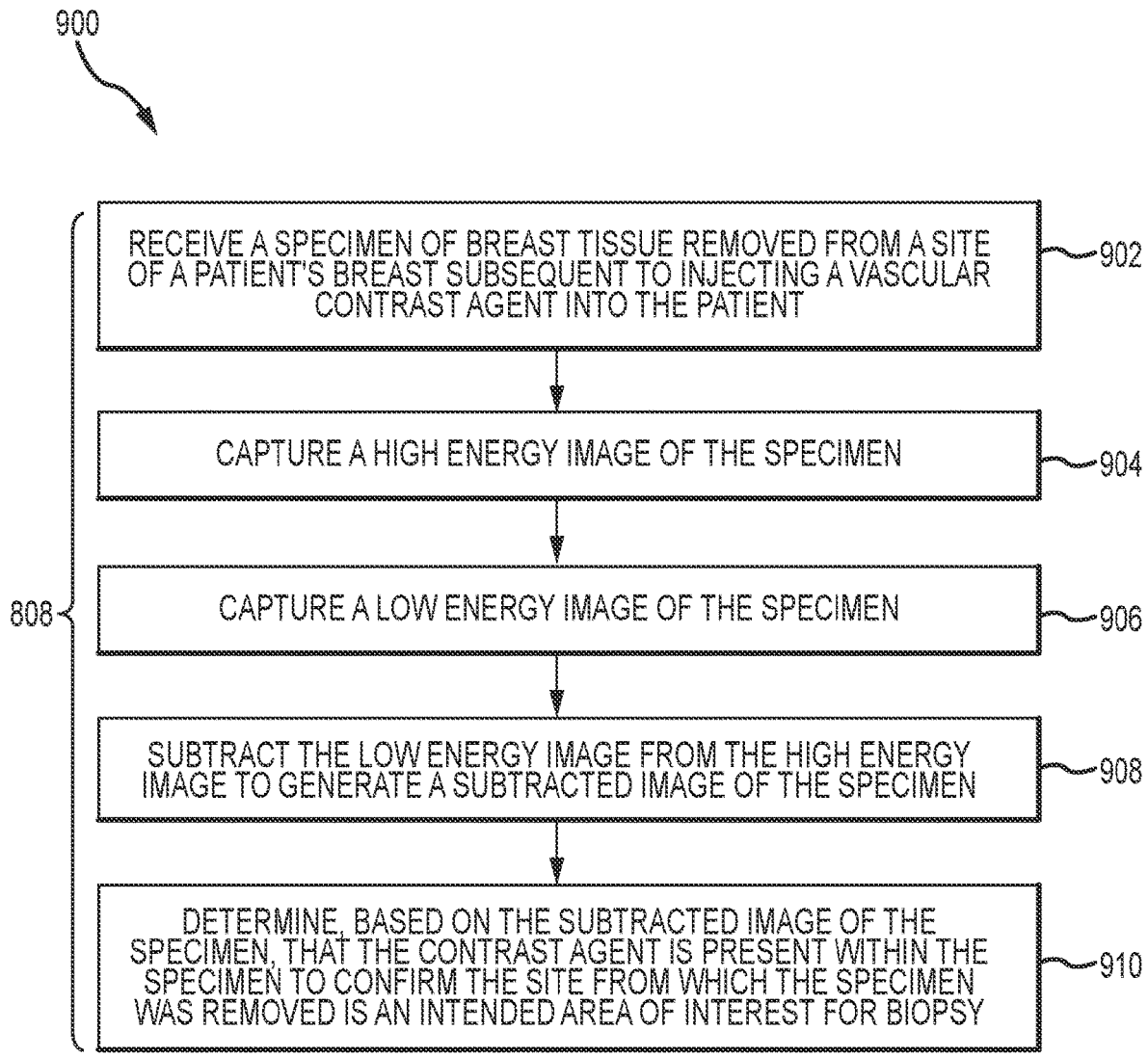
FIG. 9 is an example method for confirming tissue specimens removed using contrast-enhanced x-ray imaging.

FIG. 9 is an example method 900 for confirming tissue specimens removed using contrast-enhanced x-ray imaging. The method 900 includes operations 902, 904, 906, 908, and 910, and in some embodiments these operations can be used to at least partially perform the operation 808 of method 800.

The method 900 is performed following the removal of a specimen of breast tissue from a site of a patient's breast. The method 900 may be performed by a system that includes at least an image capturing system (e.g., x-ray source(s) and detector) for capturing images of the specimen, an apparatus for retaining the specimen in a particular position while the images are being captured, and an image processing system (e.g., an image processor) for analyzing the captured images to confirm the specimen was removed from the intended site. In some examples, the method 900 may be performed by a same breast imaging system that performs contrast-enhanced imaging of the patient's breast prior to biopsy to locate the site for biopsy and position a biopsy device relative to the site, such as system 100 shown and described with reference to at least FIGS. 1-4. Additionally or alternatively, the method 900 may be performed by a specimen imaging system separate from the breast imaging system, such as the system 200 shown and described with reference to FIGS. 5-7.

At operation 902, the specimen is received at and retained by the apparatus. The apparatus is positioned relative to an x-ray source and a detector of the image processing system such that the specimen retained by the apparatus is in a path of x-ray beams emitted from the x-ray source toward the detector. When the specimen is removed from the body, blood flow stops causing the contrast agent that was administered to the patient at operation 802 and collected around the lesion to be effectively captured within the specimen, and therefore present within the specimen (e.g., if the lesion was included in the core sample of breast tissue removed as the specimen).

At operation 904, a high energy image of the specimen is captured. For example, the x-ray source may emit high energy x-ray beams toward the detector. A value of the high energy x-ray beams may be dependent on a type of the contrast agent and an associated k-edge. In one example, the contrast agent may be an iodine based contrast agent, and the high energy x-ray beams may be above the k-edge of iodine, which is approximately 33.2 kiloelectronvolts (keV). At this higher energy above the k-edge of the contrast agent, the absorption of x-rays is increased by the contrast agent causing the contrast agent to be opaque in the high energy image.

At operation 906, a low energy image of the specimen is captured. For example, the x-ray source may emit low energy x-ray beams toward the detector, where a value of the low energy x-ray beams may similarly be dependent on a type of the contrast agent and associated k-edge. Continuing the above-example, when the contrast agent is an iodine based contrast agent, the low energy x-ray beams may be below the k-edge of iodine. At this lower energy, the contrast agent is translucent.

At operation 908, the low energy image is subtracted from the high energy image to generate a subtracted image of the specimen. In some examples, prior to the subtracting, a weighting factor may be applied to the low energy image to generate a weighted low energy image, and the weighted low energy image may be subtracted from the high energy image.

In further examples, the subtraction performed may be a weighted subtraction of a logarithmic transform of the high and low energy images. For example, initial image data for the high and low energy images that is received from the detector of the image capturing system may be in a raw format, such as pixels, where each of the pixels have a value. The image data for each of the high and low energy images may then be logarithmically transformed, causing the pixel values to be replaced by the respective logarithm. The logarithmically transformed image data for the high and low energy images may then be used for the subtraction operation. In additional examples, the logarithmic transform of the low energy image may be weighted.

In yet further examples, prior to the subtracting, a first gain controlled image may be generated from the high energy image and a second gain controlled image may be generated from the low energy image, where the second gain controlled image may be subtracted from the first gain controlled image to generate the subtracted image of the specimen.

As previously discussed, initial image data that is received from the detector of the image capturing system may be in a raw format, such as pixels. For example, the detector may include a plurality of pixels, and there may be inherent differences (e.g., different amplification gains and offsets) in the response of different pixels to the x-ray beam detected at the detector. In some examples, there are variances between pixel values that the pixels provide, even when exposed to the same x-ray input. To equalize or correct for the variances in pixel values, gain calibration and image correction techniques may be employed. For example, a first gain map may be generated and applied to the high energy image to generate the first gain controlled image. Similarly, a second gain map may be generated and applied to the low energy image to generate the second gain controlled image. Then at operation 908, the second gain controlled image may be subtracted from the first gain controlled image to generate the subtracted image of the specimen. In some examples, the subtraction may be a weighted subtraction of a logarithmic transform of the first and second first gain controlled images.

As one example of gain calibration, a gain map may be generated on a pixel-by-pixel basis to equalize or correct for the variances in pixel values recorded in the initial image data. For example, in an initial captured image (e.g., an image captured prior to the high and/or low energy image), a median pixel intensity value for all the pixels of the detector may be determined. For each individual pixel, a ratio of the median intensity value to a value of the respective pixel may yield a coefficient that is applied to the respective pixel to correct the respective pixel (e.g., to equalize the intensity value of the pixel each of the other pixels). The collection of those coefficients for each pixel may be referred to as a gain map. In some examples, a new gain map may be generated at predetermined time intervals. These techniques are provided merely as examples, and those having skill in the art will recognize and understand additional or different techniques for generating a gain map.

At operation 910, a determination that the contrast agent is present within the specimen is made based on the subtracted image, which confirms the site from which the specimen was remove is an intended area of interest for biopsy. For example, based on k-edge properties of the contrast agent, at high x-ray energies, the contrast agent is opaque, while at low x-ray energies the contrast agent is translucent. Therefore, the subtraction of the low energy image from the high energy image generates a subtracted image in which only the contrast agent remains. As previously discussed, the contrast agent administered into the patient's blood stream may be found in increased concentrations near (e.g., surrounding) the lesion due to the abnormal vascularity of the lesion, and therefore a presence or visibility of the contrast agent in the subtracted image is indicative of a correct area of tissue being removed. The confirmed specimen may then be sent for diagnostic evaluation.

Figure 10:
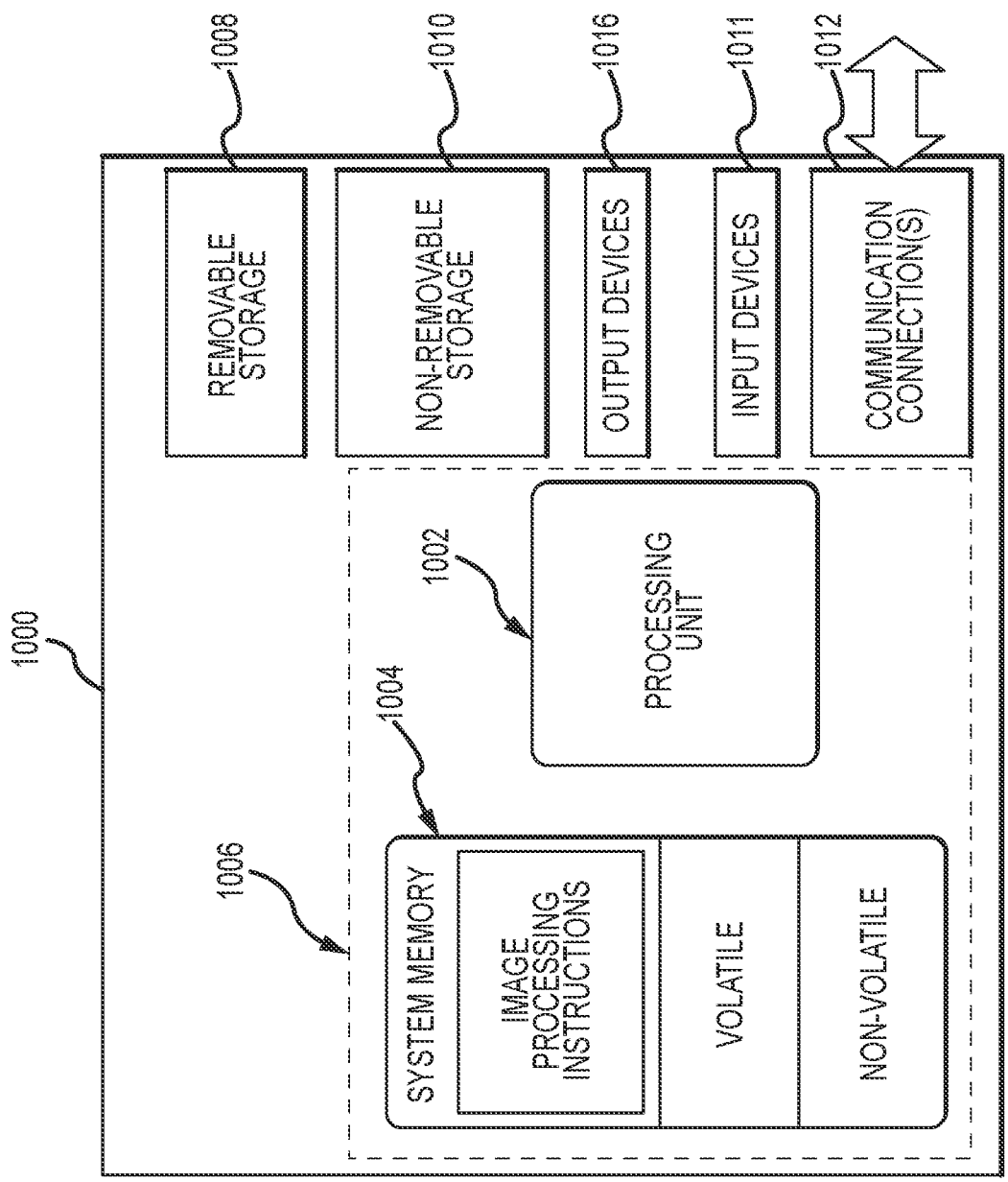
FIG. 10 illustrates one example of a suitable operating environment in which one or more of the present examples can be implemented.

FIG. 10 illustrates one example of a suitable operating environment 1000 in which one or more of the present embodiments can be implemented. This operating environment may be incorporated directly into the imaging systems disclosed herein, or may be incorporated into a computer system discrete from, but used to control, the imaging systems described herein. This is only one example of a suitable operating environment and is not intended to suggest any limitation as to the scope of use or functionality. Other computing systems, environments, and/or configurations that can be suitable for use include, but are not limited to, imaging systems, personal computers, server computers, hand-held or laptop devices, multiprocessor systems, microprocessor-based systems, programmable consumer electronics such as smart phones, network PCs, minicomputers, mainframe computers, tablets, distributed computing environments that include any of the above systems or devices, and the like.

In its most basic configuration, operating environment 1000 typically includes at least one processing unit 1002 and memory 1004. Depending on the exact configuration and type of computing device, memory 1004 (storing, among other things, instructions to perform the image acquisition and processing methods disclosed herein) can be volatile (such as RAM), non-volatile (such as ROM, flash memory, etc.), or some combination of the two. This most basic configuration is illustrated in FIG. 10 by dashed line 10006. Further, environment 1000 can also include storage devices (removable, 1008, and/or non-removable, 1010) including, but not limited to, magnetic or optical disks or tape. Similarly, environment 1000 can also have input device(s) 1014 such as touch screens, keyboard, mouse, pen, voice input, etc., and/or output device(s) 10110 such as a display, speakers, printer, etc. Also included in the environment can be one or more communication connections 1012, such as LAN, WAN, point to point, Bluetooth, RF, etc.

Operating environment 1000 typically includes at least some form of computer readable media. Computer readable media can be any available media that can be accessed by processing unit 1002 or other devices comprising the operating environment. By way of example, and not limitation, computer readable media can comprise computer storage media and communication media. Computer storage media includes volatile and nonvolatile, removable and non-removable media implemented in any method or technology for storage of information such as computer readable instructions, data structures, program modules or other data. Computer storage media includes, RAM, ROM, EEPROM, flash memory or other memory technology, CD-ROM, digital versatile disks (DVD) or other optical storage, magnetic cassettes, magnetic tape, magnetic disk storage or other magnetic storage devices, solid state storage, or any other tangible medium which can be used to store the desired information. Communication media embodies computer readable instructions, data structures, program modules, or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of the any of the above should also be included within the scope of computer readable media. A computer-readable device is a hardware device incorporating computer storage media.

The operating environment 1000 can be a single computer operating in a networked environment using logical connections to one or more remote computers. The remote computer can be a personal computer, a server, a router, a network PC, a peer device or other common network node, and typically includes many or all of the elements described above as well as others not so mentioned. The logical connections can include any method supported by available communications media. Such networking environments are commonplace in offices, enterprise-wide computer networks, intranets and the Internet.

The examples described herein may be employed using software, hardware, or a combination of software and hardware to implement and perform the systems and methods disclosed herein. Although specific devices have been recited throughout the disclosure as performing specific functions, one of skill in the art will appreciate that these devices are provided for illustrative purposes, and other devices may be employed to perform the functionality disclosed herein without departing from the scope of the disclosure.

This disclosure describes some examples of the present technology with reference to the accompanying drawings, in which only some of the possible examples were shown. Other aspects may, however, be embodied in many different forms and should not be construed as limited to the examples set forth herein. Rather, these examples were provided so that this disclosure was thorough and complete and fully conveyed the scope of the possible examples to those skilled in the art. Further, as used herein and in the claims, the phrase "at least one of element A, element B, or element C" is intended to convey any of: element A, element B, element C, elements A and B, elements A and C, elements B and C, and elements A, B, and C.

Although specific examples are described herein, the scope of the technology is not limited to those specific examples. One skilled in the art will recognize other examples or improvements that are within the scope and spirit of the present technology. Therefore, the specific structure, acts, or media are disclosed only as illustrative examples. The scope of the technology is defined by the following claims and any equivalents therein.

What is claimed is:

1. A method for confirming tissue specimens removed using contrast-enhanced x-ray imaging, the method comprising:
    receiving a specimen of breast tissue removed from a site of a patient's breast subsequent to an injection of a vascular contrast agent into the patient;
    capturing a high energy image of the specimen;
    capturing a low energy image of the specimen;
    subtracting the low energy image from the high energy image to generate a subtracted image of the specimen; and
    determining, based on the subtracted image of the specimen, that the contrast agent is present within the specimen to confirm the site from which the specimen was removed is an intended area of interest for biopsy.

2. The method of claim 1, wherein subtracting the low energy image from the high energy image to generate the subtracted image of the specimen further comprises:
    applying a weighting factor to the low energy image to generate a weighted low energy image; and
    subtracting the weighted low energy image from the high energy image.

3. The method of claim 1, wherein subtracting the low energy image from the high energy image to generate the subtracted image of the specimen further comprises:
    prior to the subtracting, generating a first gain controlled image from the high energy image and a second gain controlled image from the low energy image; and
    subtracting the second gain controlled image from the first gain controlled image to generate the subtracted image of the specimen.

4. The method of claim 1, wherein the contrast agent is opaque in the high energy image of the specimen and the contrast agent is translucent in the low energy image of the specimen such that when the low energy image is subtracted from the high energy image, the presence of the contrast agent in the specimen is visible in the subtracted image of the specimen.

5. The method of claim 1, wherein the intended area of interest for the biopsy is an area including at least a portion of potentially abnormal breast tissue.

6. A system for confirming tissue specimens removed using contrast-enhanced x-ray imaging, the system comprising:
    an image capturing system comprising at least an x-ray source and a detector for imaging a specimen of breast tissue removed during a biopsy from a site of a patient's breast subsequent to an injection of a vascular contrast agent into the patient;
    an apparatus for retaining the specimen of breast tissue after removal, the apparatus positioned relative to the x-ray source and the detector to enable the image capturing system to capture images of the specimen; and
    an image processing system communicatively coupled to the image capturing system, the image processing system including at least:
    a processor; and
    a memory coupled to the processor and storing instructions, that when executed by the processor, cause the processor to:
        receive, from the image capturing system, a captured high energy image of the specimen;
        receive, from the image capturing system, a captured low energy image of the specimen;
        subtract the low energy image from the high energy image to generate a subtracted image of the specimen; and
        determine, based on the subtracted image of the specimen, the contrast agent is present within the specimen to confirm the site from which the specimen was removed is an intended area of interest for the biopsy.

7. The system of claim 6, wherein the system is a breast imaging system, and the image capturing system is further operable to image the patient's breast subsequent to the injection of the vascular contrast agent and prior to the biopsy to one or more of locate the site and position a biopsy device relative to the site.

8. The system of claim 7, wherein the image capturing system comprises a single x-ray source.

9. The system of claim 8, wherein, when the x-ray source is the single x-ray source, the image capturing system further comprises one or more filters to enable the image capturing system to image both the patient's breast and the specimen, and capture both the high energy and low energy images.

10. The system of claim 7, wherein the apparatus is one or more of:
a specimen container positioned on the breast imaging system;
a specimen container that is removably coupleable to the breast imaging system and independently rotatable relative to the x-ray source; and
a reservoir of a vacuum assisted biopsy assembly that is independently positionable relative to the x-ray source and the detector.

11. The system of claim 6, wherein the system is a specimen imaging system separate from a breast imaging system.

12. The system of claim 11, wherein the image capturing system comprises at least two x-ray sources, a first of the at least two x-ray sources operable to emit an x-ray beam at a high energy to capture the high energy image of the specimen, and a second of the at least two x-ray sources operable to emit an x-ray beam at a low energy to capture the low energy image of the specimen.

13. The system of claim 11, wherein the apparatus is comprised of a first positioning member and a second positioning member that surround the specimen and are secured to one another to retain the specimen therebetween.

14. The system of claim 6, wherein the contrast agent is opaque in the high energy image of the specimen and the contrast agent is translucent in the low energy image of the specimen such that when the low energy image is subtracted from the high energy image, the presence of the contrast agent in the specimen is visible in the subtracted image of the specimen.

15. A breast imaging system for confirming tissue specimens removed using contrast-enhanced x-ray imaging, the breast imaging system comprising:
an image capturing system comprising at least an x-ray source, one or more filters, and a detector, the image capturing system operable to:
subsequent to an injection of a vascular contrast agent into the patient and prior to a biopsy, capture a high energy image and a low energy image of a patient's breast to one or more of locate a site for the biopsy and position a biopsy device relative to the site; and
upon removal of a specimen of breast tissue from the site during the biopsy, capture a high energy image and a low energy image of the specimen;
an apparatus for retaining the specimen upon removal, the apparatus positioned relative to the x-ray source and the detector to enable the image capturing system to capture the high energy image and the low energy image of the specimen; and
an image processing system communicatively coupled to the image capturing system, the image processing system including at least:
a processor; and
a memory coupled to the processor and storing instructions, that when executed by the processor, cause the processor to:
receive, from the image capturing system, the captured high energy image of the specimen;
receive, from the image capturing system, the captured low energy image of the specimen;
subtract the low energy image from the high energy image to generate a subtracted image of the specimen; and
determine, based on the subtracted image of the specimen, that the contrast agent is present within the specimen to confirm the site from which the specimen was removed is an intended area of interest for the biopsy.

16. The breast imaging system of claim 15, wherein at least one of the one or more filters is a specimen imaging filter implemented to enable imaging of the specimen that comprises at least one aperture defined therein, and the specimen imaging filter blocks a portion of an emitted x-ray beam from the x-ray source so that the at least one aperture defines a path of the emitted x-ray beam towards the detector.

17. The breast imaging system of claim 15, wherein the one or more filters further comprise a high energy acquisition filter to enable capture of the high energy images.

18. The breast imaging system of claim 15, further comprising a filter assembly including a plurality of filter slots, wherein each of the one or more filters is disposed within a slot of the plurality of filter slots.

19. The breast imaging system of claim 16, wherein the apparatus is one or more of:
a specimen container positioned on the breast imaging system;
a specimen container that is removably coupleable to the breast imaging system and independently rotatable relative to the x-ray source; and
a reservoir of a vacuum assisted biopsy assembly that is independently positionable relative to the x-ray source and the detector.

20. The breast imaging system of claim 16, wherein the contrast agent is opaque in the high energy image of the specimen and the contrast agent is translucent in the low energy image of the specimen such that when the low energy image is subtracted from the high energy image, the presence of the contrast agent in the specimen is visible in the subtracted image of the specimen.

* * * * *